(12) United States Patent
Lee et al.

(10) Patent No.: US 7,803,783 B2
(45) Date of Patent: Sep. 28, 2010

(54) USE OF WNT INHIBITORS TO AUGMENT THERAPEUTIC INDEX OF CHEMOTHERAPY

(75) Inventors: Mark Lee, Los Altos Hills, CA (US); Calvin Jay Kuo, Stanford, CA (US); Tannishtha Reya, Chapel Hill, NC (US); Irving L. Weissman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 285 days.

(21) Appl. No.: 11/707,386

(22) Filed: Feb. 16, 2007

(65) Prior Publication Data

US 2008/0075714 A1    Mar. 27, 2008

Related U.S. Application Data

(63) Continuation-in-part of application No. 10/729,548, filed on Dec. 5, 2003, now abandoned.

(60) Provisional application No. 60/431,655, filed on Dec. 6, 2002, provisional application No. 60/779,897, filed on Mar. 6, 2006.

(51) Int. Cl.
*A61K 31/713* (2006.01)
(52) U.S. Cl. ............... 514/44 R; 435/455; 435/375; 514/12
(58) Field of Classification Search ............... None
See application file for complete search history.

(56) References Cited

U.S. PATENT DOCUMENTS

| | | | |
|---|---|---|---|
| 5,851,984 A | 12/1998 | Matthews et al. | |
| 6,465,249 B2 | 10/2002 | Reya et al. | |
| 2002/0004241 A1 | 1/2002 | Reya et al. | |

FOREIGN PATENT DOCUMENTS

| | | |
|---|---|---|
| CA | 2467258 A1 | 5/2003 |
| WO | 0152649 | 7/2001 |

OTHER PUBLICATIONS

Reya and Clevers 2005, Nature 434:843-850.*
Suzuki et al., 2004, Nature Genetics 36:417-422.*
CAPLUS Accession No. 2003:397105, Abstract.
Dasgupta et al., Multiple Roles for Activated LEF/TCF Transcription Complexes During Hair Follicle Development and Differentiation, Development, 1999, 126: 4557-4568.
Xu et al., WISP-1 is a WNT-1-and β-Catenin-Responsive Oncogene, Genes & Dev., 2000, 14: 585-595.
Zhu et al., β-Catenin Signalling Modulates Proliferative Potential of Human Epidermal Keratinocytes Independently of Intercellular Adhesion, Development, 1999, 126: 2285-2298.
Bhanot et al., A New Member of the Frizzled Family From Drosphila Functions as a Wingless Receptor, Nature, 1996, 382: 225-30.
Eastman et al., Regulation of LEF-1/TCF Transcription Factors by WNT and Other Signals, Curr. Opin. Cell. Biol., 1999, 11(2): 233-40.
Willert et al., β-Catenin: A Key Mediator of WNT Signaling, Curr. Opin. Gen. Dev., 1998, 8(1): 95-102.
Huelsken et al., New Aspects of WNT Signaling Pathways in Higher Vertebrates, Current Opinion in Gen. & Dev. Current Biol. LTD, 2001, 11(5): 547-553.
Kielman et al., APC Modulates Embryonic Stem-Cell Differentiation by Controlling the Dosage of Beta-Catenin Signaling, Nature Gen., 2002, 32(4): 594-605.
Korinek et al., Depletion of Epithelial Stem-Cell Compartments in the Small Intestine of Mice Lacking Tcf-4, Nature Gen., 1998, 19(4): 379-383.
Plescia et al., Genomic Expression Analysis Implicates WNT Signaling Pathway and Extracellular Matrix Alterations in Hepatic Specification and Differentiation of Murine Hepatic Stem Cells, 2001, 68(4-5): 254-269.
Wong et al., Selection of Multipotent Stem Cells During Morphogenesis of Small Intestinal Crypts of Lieberkuhn is Perturbed by Stimulation of Lef-1/Beta-Catenin Signaling, J. of Biol. Chem., 2002, 277(18): 15843-15850.
Gregorieff, Alex et al., "Express Pattern of Wnt Signaling Components in the Adult Intestine", Gastroenterology, 2005, 129:626-638.
Kim, Kyung-Ah et al., "Mitogenic Influence of Human R-Spondin1 on the Intestinal Epithelium", Science, Aug. 19, 2005, Reports, vol. 309, pp. 1256-1259, www.sciencemag.org.

* cited by examiner

*Primary Examiner*—Gary B. Nickol
*Assistant Examiner*—Daniel C Gamett
(74) *Attorney, Agent, or Firm*—Bozicevic, Field & Francis LLP; Pamela J. Sherwood

(57) ABSTRACT

Methods and compositions are provided for the protection of normal cells from cytoreductive therapy that target proliferating cells, by administering an inhibitor of Wnt signaling pathways. Wnt signaling is critically important for homeostasis of the epithelial lining of the adult intestine and other proliferating normal adult tissues.

3 Claims, 9 Drawing Sheets

USE OF WNT INHIBITORS TO AUGMENT THERAPEUTIC INDEX OF CHEMOTHERAPY

This invention was made with Government support under contract R01 DK069989-01 awarded by the National Institutes of Health. The Government has certain rights in this invention.

BACKGROUND OF THE INVENTION

Wnt proteins form a family of highly conserved secreted signaling molecules that regulate cell-to-cell interactions during embryogenesis. Wnt genes and Wnt signaling are also implicated in cancer. Insights into the mechanisms of Wnt action have emerged from several systems: genetics in *Drosophila* and *Caenorhabditis elegans*; biochemistry in cell culture and ectopic gene expression in *Xenopus* embryos. Many Wnt genes in the mouse have been mutated, leading to very specific developmental defects. As currently understood, Wnt proteins bind to receptors of the Frizzled family on the cell surface. Through several cytoplasmic relay components, the signal is transduced to beta-catenin, which then enters the nucleus and forms a complex with TCF to activate transcription of Wnt target genes. Expression of Wnt proteins varies, but is often associated with developmental process, for example in embryonic and fetal tissues.

The exploration of physiologic functions of Wnt proteins in adult organisms has been hampered by functional redundancy and the necessity for conditional inactivation strategies. Dickkopf-1 (Dkk1) has been recently identified as the founding member of a family of secreted proteins that potently antagonize Wnt signaling (see Glinka et al. (1998) *Nature* 391:357-62; Fedi et al. (1999) *J Biol Chem* 274: 19465-72; and Bafico et al. (2001) *Nat Cell Biol* 3:683-6).

Signaling in the pathway is believed to be initiated by the secreted wnt proteins, which bind to a class of seven-pass transmembrane receptors encoded by the frizzled genes. Activation of the receptor leads to the phosphorylation of the disheveled protein which, through its association with axin, prevents glycogen synthase kinase 3beta (GSK3beta) from phosphorylating critical substrates. In vertebrates, the inactivation of GSK3beta might result from its interaction with Frat-1. The GSK3beta substrates include the negative regulators axin and APC, as well as β-catenin itself. Unphosphorylated β-catenin escapes recognition by β-TRCP, a component of an E3 ubiquitin ligase, and translocates to the nucleus where it engages transcription factors such as TCF and LEF. Additional components in the pathway include casein kinases I and II, both of which have been proposed to phosphorylate disheveled. The serine/threonine phosphatase PP2A associates with axin and APC. In the absence of wnt, GSK3beta phosphorylates APC and axin, increasing their binding affinities for β-catenin, which too is phosphorylated by GSK3beta, marking it for destruction. In the presence of wnt, FRAT prevents GSK3beta from phosphorylating its substrates, and β-catenin is stabilized. Casein kinase1epsilon (CK1epsilon) binds to and phosphorylates disheveled (dvl), modulating the FRAT1/GSK3beta interaction.

The wnt ligands, of which there are at least 16 members in vertebrates, are secreted glycoproteins that can be loosely categorized according to their ability to promote neoplastic transformation. There are also numerous wnt receptors. At least 11 vertebrate frizzled genes have been identified. In addition to the frizzled receptors, there exists a family of secreted proteins bearing homology to the extracellular cysteine-rich domain of frizzled. The so-called secreted frizzled-related proteins (sFRP) bind to the wnt ligands, thereby exerting antagonistic activity when overexpressed in wnt signaling assays. The vertebrate sFRPs, like the frizzled proteins, exhibit functional specificity with respect to the various wnts.

Mutations in several genes are associated with tumorigenicity, including b-catenin, APC and Axin. Mutations in the β-catenin gene (CTNNb1) affecting the amino-terminal region of the protein make it refractory to regulation by APC. These mutations affect specific serine and threonine residues, and amino acids adjacent to them, that are essential for the targeted degradation of β-catenin. These regulatory sequence in β-catenin are mutated in a wide variety of human cancers as well as in chemically and genetically induced animal tumors. Axin is regarded as a tumor suppressor, which when mutated alters the Wnt signaling pathway.

APC is a tumor suppressor in human cancers and its mutation relates strongly to the regulation of β-catenin. The spectrum of APC mutations, which typically truncate the protein, suggest selection against β-catenin regulatory domains, albeit not necessarily against β-catenin binding. The presence of axin binding sites are critical to APC in the regulation of beta-catenin levels and signaling in cultured cells. In colorectal cancer, the vast majority of tumors contain APC mutations, although the overall frequency of β-catenin mutations is quite low. When colorectal tumors lacking APC mutations were analyzed separately, the likelihood of finding a CTNNb1 mutation was greatly increased.

Aggressive fibromatosis, otherwise known as desmoid tumor, is a locally invasive fibrocytic growth that occurs with increased incidence in patients with familial adenomatous polyposis coli (FAP). FAP individuals carry APC mutations in their germline and present with multiple intestinal adenomas at an early age. Desmoids also occur sporadically and, with the exception of colorectal cancer, represent a rare example of biallelic inactivation of APC in individuals without a pre-existing germline mutation in APC. Mutations in CTNNb1 have also been detected in sporadic desmoid tumors.

Several mutations in CTNNb1 were recently identified in gastric cancers, which occur with increased incidence in FAP patients. In one study, 27% of intestinal type gastric cancers harbored mutations in β-catenin. Hepatoblastoma also occurs with increased incidence in FAP individuals. In three separate studies, mutations in β-catenin were identified at high frequency in hepatoblastoma. Thyroid cancers also occur with increased incidence in FAP and a high frequency of CTNNb1 mutations has been reported for anaplastic thyroid cancers. Hepatocellular carcinoma (HCC) is one of the most common tumors harboring mutations in the wnt pathway. The frequency of CTNNb1 mutations in hepatocellular carcinoma (HCC) was ~20% overall and may be higher for HCCs associated with hepatitis C virus. Some cancers, such as endometrial ovarian tumors, do not occur with increased incidence in patients with FAP, yet they contain activating mutations in CTNNb1. The CTNNb1 mutations associated with ovarian cancer appeared to be confined to the endometrioid subtype. Additional types of cancers with CTNNb1 mutations include melanoma and prostate. The highest percentage of CTNNb1 mutations occurs in a common skin tumor known as pilomatricomas.

Conventional cytotoxic chemotherapy for cancer targets rapidly dividing cells within tumors. Correspondingly, such chemotherapy is generally limited by its effects on rapidly dividing cells in normal tissues in patients, such as those in the hematopoietic system, the lining of the gastrointestinal tract, and the skin.

In another example, ionizing radiation (IR) is used to treat about 60% of cancer patients, by depositing energy that injures or destroys cells in the area being treated. Radiation injury to cells is nonspecific, with complex effects on DNA. The efficacy of therapy depends on cellular injury to cancer cells being greater than to normal cells. Radiotherapy may be used to treat every type of cancer. Some types of radiation therapy involve photons, such as X-rays or gamma rays. Another technique for delivering radiation to cancer cells is internal radiotherapy, which places radioactive implants directly in a tumor or body cavity so that the radiation dose is concentrated in a small area.

Radiotherapy may be used in combination with additional agents. Radiosensitizers make the tumor cells more likely to be damaged, and radioprotectors protect normal tissues from the effects of radiation. Hyperthermia is also being studied for its effectiveness in sensitizing tissue to radiation.

A method to prevent toxicity to normal tissues while preserving efficacy against tumor cells would augment the therapeutic index of chemotherapy and radiation therapy and limit the adverse side effects of such treatments for patients. In addition, the availability of this type of technology would permit the safe use of higher doses of therapy with enhanced anti-tumor effects. At present effective methods of this type have not been described and none have entered widespread clinical use. The present invention is designed to meet this need.

Related Publications

Wnts act by binding the receptors of the Frizzled family (Bhanot et al. (1996) *Nature* 382:225-30) in association with the low-density lipoprotein receptor related proteins (LRP). In the absence of a Wnt signal, the serine/threonine kinase GSK-3β phosphorylates beta-catenin, targeting it for ubiquitination and degradation by proteosomes. Binding of Wnt proteins to their receptors leads to beta-catenin stabilization and accumulation in the cytosol (Willert & Nusse (1998) *Curr Opin in Gen Dev* 8:95-102). Beta-catenin can then translocate to the nucleus, where it binds to members of the LEF-1/TCF family of transcription factors and causes induction of target genes Eastman & Grosschedl (1999) *Curr Opin Cell Biol* 11:233-40).

The use of β-catenin in the expansion of stem cells is discussed in U.S. Pat. No. 6,465,249. The use of wnt to stimulate hematopoietic stem cells is proposed in U.S. Pat. No. 5,851,984. Protection is stem cells is discussed in US-2004-0171559-A1.

SUMMARY OF THE INVENTION

Methods and compositions are provided for cytoreductive treatment of tumors. Tumors of interest proliferate independently of external Wnt signaling, and may comprise tumorigenic mutations in components of the Wnt signaling pathway, particularly β-catenin, axin and APC. In the methods of the invention, an inhibitor of wnt signaling is administered to an individual prior to treatment with a cytoreductive therapy, usually a cytoreductive therapy that is cell cycle specific, e.g. S-phase specific, e.g. chemotherapy with S-phase specific agents, radiation therapy, etc. Proliferating cells dependent on extracellular Wnt, e.g. hematopoietic stem and progenitor cells; gut epithelial cells; etc. are rendered non-proliferative by the inhibitor of Wnt signaling, and thus are protected from the cytoreductive therapy. The methods may thus permit higher doses of therapy than would otherwise be possible due to toxicity limitation.

Wnt inhibitors of interest interfere with the interaction between soluble, extracellular wnt proteins, and the frizzled receptors that are present on the surface of normal cells, particularly on the surface of gut epithelia and hematopoietic cells. Such agents include, without limitation, soluble frizzled polypeptides comprising the wnt binding domains; soluble frizzled related polypeptides; wnt specific antibodies; frizzled specific antibodies; and other molecules capable of blocking extracellular wnt signaling.

In one embodiment of the invention, the protective agents have specificity for wnt proteins that interact with stem cells, particularly hematopoietic stem cells. In another embodiment of the invention, the protective agents have specificity for frizzled proteins expressed on the surface of stem cells, particularly by hematopoietic stem cells. There is overlap in the specificity of wnt proteins and frizzled receptors, and in some embodiments of the invention, the protective agents broadly interacts with multiple wnt proteins. Methods are provided for screening agents in vivo and in vitro for efficacy as protective agents.

In one embodiment of the invention, β-catenin activation from extracellular signaling is temporarily blocked by administration of a protective agent, which administration is performed before or during administration of a cytotoxic agent that targets proliferating cells. Cytotoxic agents that target proliferating cells include chemotherapeutic drugs used in the treatment of cancer. In one aspect, the cytotoxic agent is an inhibitor of enzymes involved in DNA synthesis, e.g. topoisomerases; polymerases, etc. In another aspect, the cytotoxic agent is an analog of a metabolite, e.g. a purine, pyrimidine or folic acid analog. In another aspect of the invention, the cytotoxic agent is an immunosuppressive agent. In another aspect, the cytotoxic agent is an antimicrobial agent.

In another embodiment of the invention, β-catenin activation from extracellular signaling is temporarily blocked by administration of a protective agent, which administration is performed before or during administration of a cytotoxic agent that targets proliferating cells, wherein at the conclusion of the chemotherapy, a dose of wnt protein effective to overcome the temporary block of stem cell proliferation is administered.

DETAILED DESCRIPTION OF THE EMBODIMENTS

Figure 1:
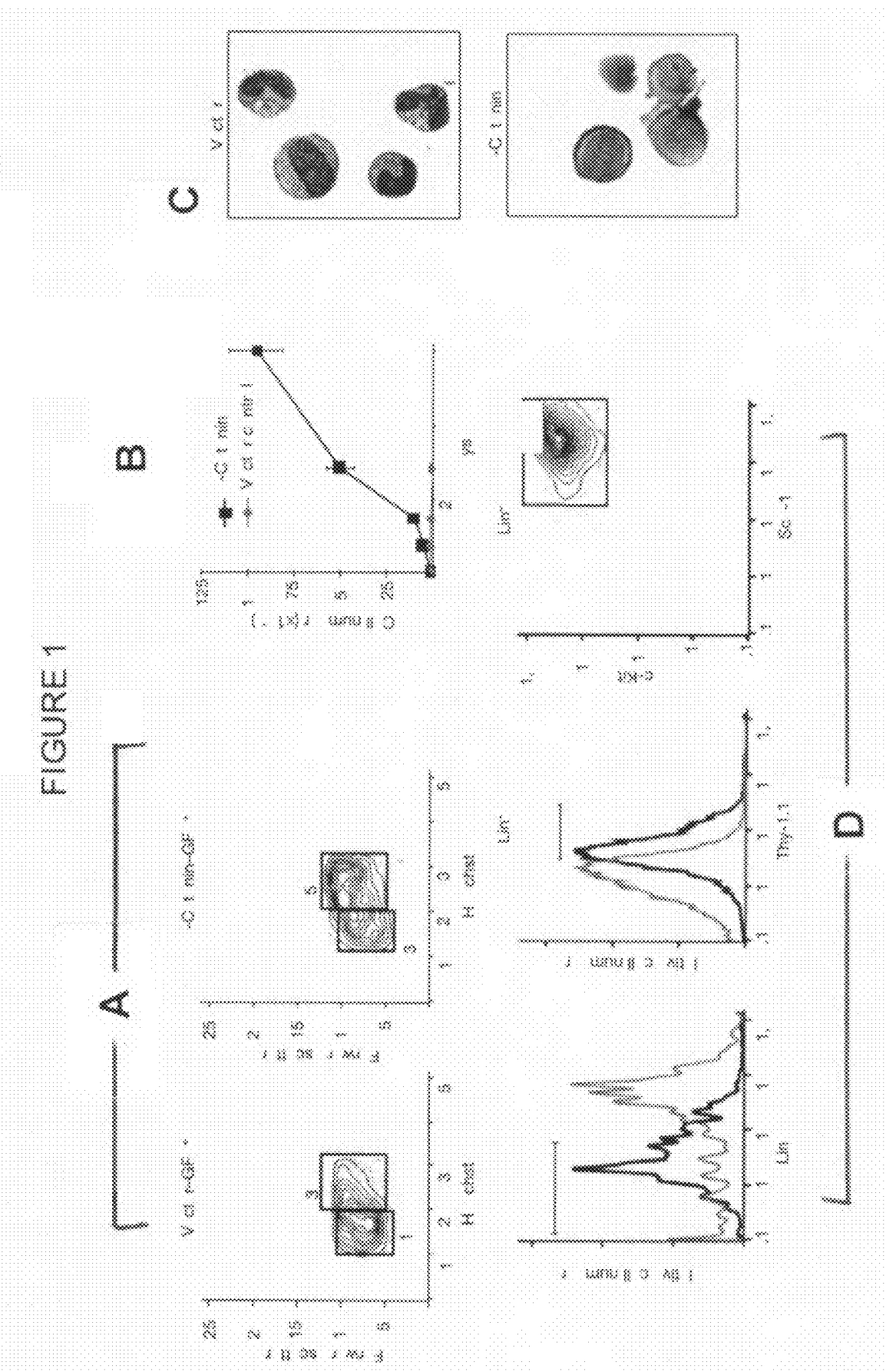
FIGS. 1A-1D. Activated β-catenin promotes growth of HSCs in vitro and maintains the immature phenotype of HSCs in long-term cultures. HSCs were infected with activated β-catenin-IRES-GFP or control GFP retrovirus, and subjected to cell cycle analysis after 60 h. a, β-catenin-infected cultures display an increased number of blasting cells (right box, S/G2/M) compared with control. b, For long-term growth studies, 10,000 infected HSCs were plated in 1 ng ml$^{-1}$ SLF and monitored over 60 days. Results are from one of five experiments. c, Giemsa staining reveals myeloid characteristics in control cells and HSC morphology (high nucleus to cytoplasm ratio) in β-catenin-infected cells. d, Control cells (grey lines) are largely lineage-positive, whereas most β-catenin-infected cells (black lines) are lineage-negative (Lin$^-$) or have low levels (left panel). β-catenin-infected Lin$^-$ cells have characteristics of HSCs, including low Thy-1.1 (middle panel), and high c-Kit and Sca-1 (right panel).

Methods and compositions are provided for the protection of normal cells from cytotoxic therapy that target proliferating cells, by administering an inhibitor of Wnt signaling pathways. Wnt signaling is critically important for homeostasis of the epithelial lining of the adult intestine and other proliferating normal adult tissues.

The wnt pathway is aberrantly activated in a number of human cancers. In the large majority of cases, constitutive Wnt pathway activation is the result of mutational inactivation of the intracellular proteins APC or Axin (which act as negative regulators of Wnt) or activation of β-catenin. For example, in human colorectal cancer, these changes in APC, Axin, or β-catenin are believed to be present in more than 85% of cases. Tumors bearing activating changes in intracellular Wnt pathway components are, by and large, insensitive to extracellular Wnt inhibition.

In certain embodiments of the invention, the patient to be treated has familial adenomatous polyposis coli (FAP). Familial adenomatous polyposis, often called FAP, is an inherited colorectal cancer syndrome. This cancer usually develops in the lower part of the digestive system, including the large intestine (colon) and rectum. People with the classic type of familial adenomatous polyposis may begin to develop multiple noncancerous (benign) polyps (growths) in the colon as early as their teenage years. The average age at which an individual develops colon cancer in classic familial adenomatous polyposis is about 39 years. Some people have a variant of the disorder, called attenuated familial adenomatous polyposis, in which polyp growth is delayed. The average age of colorectal cancer onset for attenuated familial adenomatous polyposis is about 55 years. Familial adenomatous polyposis affects about 1 in 30,000 people. Mutations in the APC gene cause both classic and attenuated familial adenomatous polyposis. Mutations in the APC gene affect the ability of the cell to maintain normal growth and function. Cell overgrowth resulting from mutations in the APC gene leads to the colon polyps seen in familial adenomatous polyposis. Although most people with mutations in the APC gene will develop colorectal cancer, the number of polyps and the time frame in which they become malignant depend on the location of the mutation in the gene.

In one embodiment of the invention, the patient to be treated has human colorectal cancer. In another embodiment, the patient has pilomatricoma. In another embodiment, the patients has aggressive fibromatosis. In another embodiment, the patient has intestinal type gastric cancer. In yet another embodiment the patient has hepatoblastoma or hepatocellular carcinoma. In another embodiment, the patient has anaplastic thyroid cancer. In another embodiment, the patient has an endometrial ovarian tumor.

Optionally, the patient is screened prior to treatment with the methods of the invention. Screening methods of interest include screening for germline or tumor associated mutations in the adenomatosis polyposis coli (APC) gene, e.g. for the diagnosis of FAP, association of a cancer with wnt signaling, etc. Many such APC mutations are known in the art, for example one may refer to Okamoto et al. (1990) Hum. Genet. 85: 595-599, among others. Selected examples of mutations in this gene include

| | |
|---|---|
| APC, 5-BP DEL, CODON 1309 | APC, 2-BP DEL, EX7 |
| APC, SER1395CYS | APC, ARG-TER, 904C-T |
| APC, 2-BP INS, CODON 1924 | APC, 1-BP DEL, EX10 |
| APC, 4-BP DEL, CODON 1962 | APC, TYR-TER, 1500T-G |
| APC, 1-BP DEL, EX15 | APC, ARG414CYS |
| APC, 4-BP DEL, EX15 | APC, ARG302TER |
| APC, ILE1307LY | APC, SER280TER |
| APC, 2-BP DEL, CODON 1538 | APC, SER713TER |
| APC, 499TER | APC, GLN1338TER |
| APC, 486TER | APC, GLY1120GLU |
| APC, 3-BP DEL | APC, GLN1067TER |
| APC, 2-BP DEL | APC, 4-BP DEL, CODON 169 |
| APC, 2-BP DEL | APC, 1-BP INS, ILE357 |
| APC, GLU1317GLN | APC, GLN541TER |
| APC, 2-BP DEL, 937GA | APC, ARG554TER |
| APC, LEU698TER | APC, ARG564TER |
| APC, 337-BP INS | APC, 1-BP INS, CODON 629 |
| APC, IVS3AS, G-A, -1 | APC, TYR935TER |
| APC, 11-BP INS, NT1060 | APC, 2-BP DEL, CODON 1465 |
| APC, 4-BP DEL, 7929TCTA | APC, 4-BP DEL, CODON 1464 |
| APC, 1-BP DEL, 3720T | APC, TRP157TER |
| APC, GLN208TER | APC, GLN215TER |
| APC, 1-BP DEL | APC, 4-BP DEL, CODON 1962 |
| APC, 56-KB DEL, EX15DEL | APC, 1-BP DEL, EX15 |
| APC, 73-KB DEL, EX15DEL | APC, 4-BP DEL, EX15 |
| APC, 5-BP DEL, NT3221 | APC, ILE1307LY |
| APC, 5-BP DEL, CODON 1309 | APC, 2-BP DEL, CODON 1538 |
| APC, SER1395CYS | APC, 499TER |
| APC, 2-BP INS, CODON 1924 | APC, 486TER |
| APC, 2-BP DEL, 937GA | APC, 3-BP DEL |
| APC, LEU698TER | APC, 2-BP DEL |
| APC, 337-BP INS | APC, 2-BP DEL |
| APC, IVS3AS, G-A, -1 | APC, GLU1317GLN |
| APC, 11-BP INS, NT1060 | APC, 1-BP DEL, 3720T |
| APC, 4-BP DEL, 7929TCTA | APC, GLN208TER |

Patients may also be screened for the presence of mutations in Axin, for example as described by Satoh et al. (2000) *Nature Genet.* 24: 245-250, herein specifically incorporated by reference.

In addition, or in combination, patients may be screened for the presence of mutations in β-catenin. Mutations in β-catenin have been found, inter alia, to be associated with colorectal cancer, hepatoblastoma, pilomatricoma, and ovarian carcinoma. Examples of mutations include CTNNB1, 3-BP DEL, SER45DEL; CTNNB1, SER33TYR; CTNNB1, THR41ALA; CTNNB1, ASP32TYR; CTNNB1, GLY34VAL; CTNNB1, ASP32GLY; CTNNB1, SER33PHE; CTNNB1, GLY34GLU; CTNNB1, SER37CYS; CTNNB1, SER37PHE; CTNNB1, THR41ILE; CTNNB1, SER37CYS; CTNNB1, SER45PHE; CTNNB1, SER45PRO and CTNNB1, ASP32TYR.

Methods of screening for the presence of mutations are well-known in the art, and may include detecting specific DNA and/or RNA sequences, e.g. by array hybridization, PCR amplification, etc.; by the detection of truncated or otherwise mutated polypeptides; and the like.

Tumor cells may also be screened for Wnt independent growth. In such a method, tumor cells of interest are contacted with a Wnt inhibitor of interest, and the proliferation of the cells, e.g. by uptake of tritiated thymidine, etc., is monitored. In certain embodiments of the invention, a candidate patient is screened for the presence of a cancer that is associated with a mutation in the Wnt signaling pathway, wherein patients having such a mutation are treated with the methods of the invention. Candidate cancers include, without limitation, those listed above.

Figure 4:
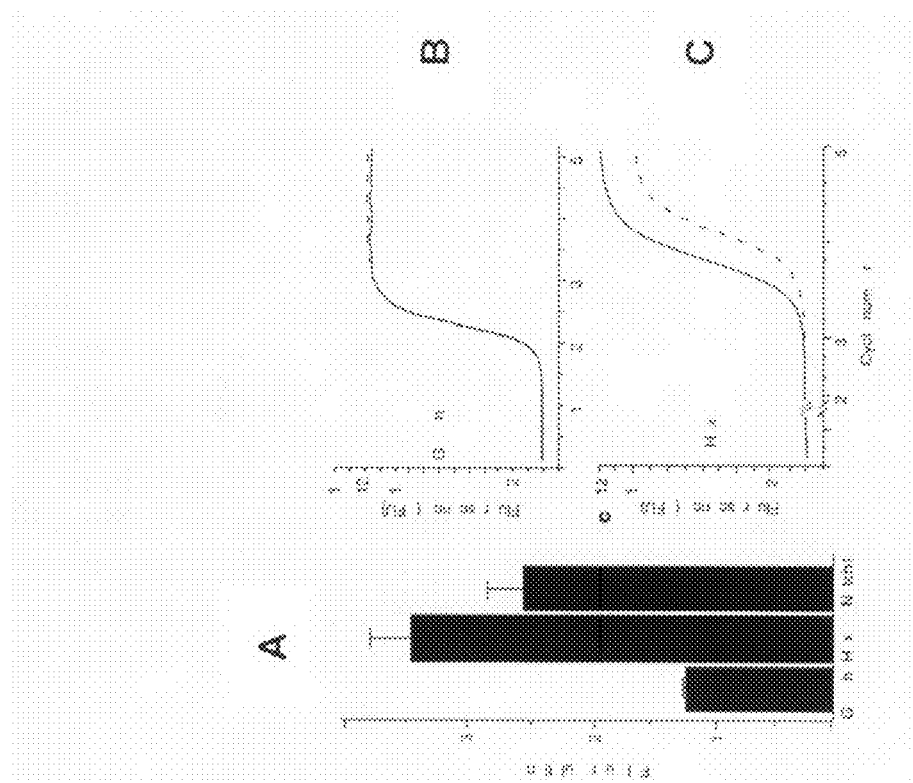
FIGS. 4A-4C. HSCs expressing β-catenin upregulate HoxB4 and Notch1. a, Purified wild-type HSCs were infected with activated β-catenin-IRES-GFP or control vector-IRES-GFP, and infected cells sorted based on GFP expression at 48 h. The RNA isolated from these cells was reverse transcribed and expression of HoxB4 and Notch1 was analyzed by real-time PCR analysis. Results are averaged over five independent PCR reactions. b, c, Representative graphs of real-time PCR analysis demonstrating equal amounts of GADPH (b) and differential amounts of HoxB4 (c) products from β-catenin-transduced HSCs (solid line) and control-transduced HSCs (dashed line). RFU, relative fluorescence units.

The present invention utilizes extracellular Wnt inhibitors to block cell cycling and growth of normal tissues while having little or no effect on tumor cells with intracellular Wnt pathway activation. Prior to initiation of chemotherapy, a Wnt inhibitor is delivered systemically for a sufficient period of time to block normal cell cycling in normal tissues, e.g. intestinal epithelium, hematopoietic cells, skin, etc. Cell-cycle specific chemotherapy is then given through conventional methods of administration, for example as shown in FIG. 4. During administration of chemotherapy, a sufficient level of systemic Wnt inhibition is maintained to ensure that normal tissues are not rapidly dividing, and thus susceptible to cytotoxic effects of chemotherapy. After completion of chemotherapy delivery and an adequate period of time to permit drug wash-out has occurred, the Wnt inhibitor is withdrawn, thus relieving the proliferative block on normal tissues and allowing resumption of normal tissue homeostasis. Administration of chemotherapy using the methods of the invention limits toxicity in normal tissues and permits dose escalation of chemotherapy, enhancing anti-tumor efficacy.

In one embodiment, definition of optimal dose and treatment duration of the Wnt inhibitor(s) in preclinical models may utilize an adenovirus technology (Ad TRE (Tetracycline response element)) which permits rigorously controlled expression of adenovirally carried transgenes under the control of the tetracycline operator/promoter system. Expression of the desired transgene engineered in the Ad TRE adenovirus utilizes co-infection with Ad tTA (tetracycline transactivator), which is an adenovirus which expresses the requisite transcription factor for the TRE system. In the absence of tetracycline (or its analog doxycycline), co-infection with Ad TRE and Ad tTA viruses results in expression of a desired transgene; the duration of expression can be precisely controlled by timed initiation of doxycycline treatment both in vitro and in vivo. The amplitude of the transgene product serum levels in vivo can be modulated by changing the Ad TRE dose, by varying the ratio of Ad TRE/Ad tTA, or by administering a titrated, low-dose of doxycycline to the experimental animals.

This system has been validated for Ad TRE Dkk1, and is known to produce robust, short-term systemic expression of Dkk1 in mice. This level of expression is capable of producing changes in the intestinal epithelium with loss of the proliferative crypts in the proximal small bowel. This system provides a rapid method for optimizing a dosing strategy for Dkk1 which satisfies the following requirements: (1) produces potent and rapid inhibition of Wnt-dependent proliferation in the gastrointestinal tract (and in other proliferating tissues), (2) persists for the duration of cytotoxic therapy (cell-cycle specific chemotherapy or radiotherapy), and (3) is of sufficiently short duration such that it does not produce significant toxicity (gastrointestinal or other). Upon establishment of such a dosing schedule using Ad TRE Dkk1, optimization of this schedule in combination with cytotoxic therapy can then proceed. Similarly, other Wnt inhibitors (with potentially different potency, pharmacokinetics, profiles of specific Wnt inhibition) can be tested in the Ad TRE system and optimized for this application. Wnt inhibitors thus validated may be evaluated as administration of purified recombinant proteins (i.e. virus-free system) in preclinical models.

For dosing in humans, recombinant Wnt inhibitors validated in pre-clinical models are tested in dose-finding studies. Such assessment may include the pharmacokinetic properties of Wnt inhibitors (including metabolism, rate of clearance, etc), the importance of specific Wnts for proliferation in a target tissue, etc. A non-invasive approach to monitoring gastrointestinal epithelial proliferation is preferred, for example using FDG-PET scanning, which monitors metabolic activity in vivo non-invasively, or other similar non-invasive functional imaging technologies. With this type of validated, non-invasive monitoring, a minimum dose Wnt inhibitor dose which effectively abolishes proliferation in vivo is determined.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Wnt polypeptide and agonists thereof. As used herein, the terms "Wnts" or "Wnt gene product" or "Wnt polypeptide" when used herein encompass native sequence Wnt polypeptides, Wnt polypeptide variants, Wnt polypeptide fragments and chimeric Wnt polypeptides. In some embodiments of the invention, the Wnt protein comprises palmitate covalently bound to a cysteine residue. A "native sequence" polypeptide is one that has the same amino acid sequence as a Wnt polypeptide derived from nature. The native sequence of human Wnt polypeptides may range from about 348 to about 389 amino acids long in their unprocessed forms, reflecting variability at the poorly conserved amino-terminus and several internal sites, contain 21 conserved cysteines, and have the features of a secreted protein. The molecular weight of a Wnt polypeptide is usually about 38-42 kD.

The term "native sequence Wnt polypeptide" includes human Wnt polypeptides. Human wnt proteins include the following: Wnt 1, Genbank reference NP_005421.1; Wnt 2, Genbank reference NP_003382.1, which is expressed in brain in the thalamus, in fetal and adult lung and in placenta; two isoforms of Wnt 2B, Genbank references NP_004176.2 and NP_078613.1. Isoform 1 is expressed in adult heart, brain, placenta, lung, prostate, testis, ovary, small intestine and colon. In the adult brain, it is mainly found in the caudate nucleus, subthalamic nucleus and thalamus. Also detected in fetal brain, lung and kidney. Isoform 2 is expressed in fetal brain, fetal lung, fetal kidney, caudate nucleus, testis and cancer cell lines. Wnt 3 and Wnt3A play distinct roles in cell-cell signaling during morphogenesis of the developing neural tube, and have the Genbank references NP_110380.1 and X56842. Wnt3A is expressed in bone marrow. Wnt 4 has the Genbank reference NP_110388.2. Wnt 5A and Wnt 5B have the Genbank references NP_003383.1 and AK013218. Wnt 6 has the Genbank reference NP_006513.1; Wnt 7A is expressed in placenta, kidney, testis, uterus, fetal lung, and fetal and adult brain, Genbank reference NP_004616.2. Wnt 7B is moderately expressed in fetal brain, weakly expressed in fetal lung and kidney, and faintly expressed in adult brain, lung and prostate, Genbank reference NP_478679.1. Wnt 8A has two alternative transcripts, Genbank references NP_114139.1 and NP_490645.1. Wnt 8B is expressed in the forebrain, and has the Genbank reference NP_003384.1. Wnt 10A has the Genbank reference NP_079492.2. Wnt 10B is detected in most adult tissues, with highest levels in heart and skeletal muscle. It has the Genbank reference NP_003385.2. Wnt 11 is expressed in fetal lung, kidney, adult heart, liver, skeletal muscle, and pancreas, and has the Genbank reference NP_004617.2. Wnt 14 has the Genbank reference NP_003386.1. Wnt 15 is moderately expressed in fetal kidney and adult kidney, and is also found in brain. It has the Genbank reference NP_003387.1. Wnt 16 has two isoforms, Wnt-16a and Wnt-16b, produced by alternative splicing. Isoform Wnt-16B is expressed in peripheral lymphoid organs such as spleen, appendix, and lymph nodes, in kidney but not in bone marrow. Isoform Wnt-16a is expressed at significant levels only in the pancreas. The Genbank references are NP_057171.2 and NP_476509.1.

Other activators of wnt signaling include compounds that bind to, and activate receptors of the Frizzled family on the cell surface, e.g. antibodies and fragments thereof, wnt mimetics and derivatives, and the like. An additional method of achieving Wnt inhibition is the neutralization of a Wnt inhibitor, i.e. the chelation of Dkk by a soluble ectodomain of Kremen1/2 or LRP5/6).

Wnt inhibitor. Wnt inhibitors are agents that downregulate expression or activity of wnt. Agents of interest may interact directly with wnt, e.g. drugs, i.e. small organis molecules, blocking antibodies, etc., or may interact with wnt associated proteins, e.g. Wnt co-receptors LRP5/6 and the transmembrane protein Kremen. A number of wnt inhibitors have been described and are known in the art, including those described above.

In one embodiment of the invention, a wnt inhibitor is provided in an amount effective to detectably inhibit the binding of extracellular wnt to frizzled present on the surface of normal cells, particularly normal gut epithelial cells. In one embodiment, the protective agent is selected from: soluble FZD CRD, including FZ8-Fc; antibodies to FZD, including Fz8; secreted frizzled-related proteins (sFRPs), antibodies to Wnt; antibodies LRP5/6; antibodies to Kremen; Dkk proteins, Soggy protein, Wise; fusions proteins comprising any of the above; derivatives of any of the above; variants of any of the above; and biologically active fragments of any of the above. In another embodiment, the protective agent is selected from FZD8 CRD, FZD CRD-IgG fusion proteins, SFRP-1, SFRP-2, SFRP-3, SFRP-4, SFRP-5, Dkk-1, Dkk-2, Dkk-3, Dkk-4, Soggy, Wise, antibodies to wnt 3A, antibodies to wnt 2B; antibodies to wnt 10B and antibodies to wnt 5A.

In one embodiment, the inhibitor blocks the activity of Fz5, Fz6 or Fz7 (see Gregorieff et al. (2005) Gastroenterology 129:626-638, herein specifically incorporated by reference).

Among the known wnt inhibitors are members of the Dickkopf (Dkk) gene family (see Krupnik et al. (1999) Gene 238(2):301-13). Members of the human Dkk gene family include Dkk-1, Dkk-2, Dkk-3, and Dkk-4, and the Dkk-3 related protein Soggy (Sgy). hDkks 1-4 contain two distinct cysteine-rich domains in which the positions of 10 cysteine residues are highly conserved between family members. Exemplary sequences of human Dkk genes and proteins are publicly available, e.g. Genbank accession number NM_014419 (soggy-1); NM_014420 (DKK4); AF177394 (DKK-1); AF177395 (DKK-2); NM_015881 (DKK3); and NM_014421 (DKK2).

Inhibitors may also include derivatives, variants, and biologically active fragments of native inhibitors. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

A "chimeric" native inhibitors polypeptide is a polypeptide comprising a polypeptide or portion (e.g., one or more domains) thereof fused or bonded to heterologous polypeptide. The chimeric polypeptide will generally share at least one biological property in common with a native sequence polypeptide. Examples of chimeric polypeptides include immunoadhesins, combine a portion of the native inhibitors polypeptide with an immunoglobulin sequence, and epitope tagged polypeptides, which comprise a native inhibitors polypeptide or portion thereof fused to a "tag polypeptide". The tag polypeptide has enough residues to provide an epitope against which an antibody can be made, yet is short enough such that it does not interfere with biological activity of the native inhibitors polypeptide. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications there Other inhibitors of wnt include Wise (Itasaki et al., (2003) Development 130(18):4295-30), which is a secreted protein. The Wise protein physically interacts with the Wnt co-receptor, lipoprotein receptor-related protein 6 (LRP6), and is able to compete with Wnt8 for binding to LRP6. Axin regulates Wnt signaling through down-regulation of beta-catenin (see Lyu et al. (2003) J Biol Chem. 278(15):13487-95).

A soluble form of the ligand binding domain (CRD) of Frizzled has been shown to inhibit wnt. The Frizzled-CRD domain has been shown to inhibit the Wnt pathway by inhibiting the binding of Wnts to the frizzled receptor (Hsieh et al. (1999) Proc Natl Acad Sci USA 96:3546-51; and Cadigan et al. (1998) Cell 93:767-77). Polypeptides of interest include Fz8, FRP5, FRP8, and the like. Similarly, SFRPs represent secreted molecules which encode Frizzled-like CRDs and thus represent soluble Wnt antagonists by functioning as soluble receptors (Krypta et al, J Cell Sci 2003 Jul. 1; 116(Pt 13):2627-34).

Inhibitors of wnt signaling also include agents that block the action of R-spondins (see Kim et al. (2005) Science 309: 1256-1259, herein specifically incorporated by reference). R-spondins have a strongly mitogenic influence on intestinal epithelium. Antagonists include dominant negative proteins, antibodies that bind to or otherwise block R-spondin activity, competitive inhibitors such as peptides, small molecules, etc., and the like.

Compound screening. Candidate inhibitors of wnt signaling may be identified by detecting the ability of an agent to affect the biological activity of wnt. A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in binding.

Compounds of interest for screening include biologically active agents of numerous chemical classes, primarily organic molecules, although including in some instances inorganic molecules, organometallic molecules, genetic sequences, etc. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Compounds are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Molecules of interest as inhibitors include specific binding members that bind to, e.g. wnt, frizzled, wnt co-receptors, and the like. The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; lipid and lipid-binding protein; etc. The specific binding pairs may include analogs, derivatives and fragments of the original specific binding member.

In a preferred embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the brain tumor protein target, a superior immune response may be elicited if the polypeptide is joined to a carrier protein, such as ovalbumin, BSA or KLH. Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. In addition, the antibodies or antigen binding fragments may be, produced by genetic engineering. Humanized, chimeric, or xenogenic human antibodies, which produce less of an immune response when administered to humans, are preferred for use in the present invention.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment" or minimal immunoglobulins may be designed utilizing recombinant immunoglobulin techniques.

For instance "Fv" immunoglobulins for use in the present invention may be produced by linking a variable light chain region to a variable heavy chain region via a peptide linker (e.g., poly-glycine or another sequence which does not form an alpha helix or beta sheet motif).

The methods of the present invention utilize inhibition of wnt signaling. In general, the effect of the agents on intestinal epithelium may be considered indicative of the wnt activity. Such activity may be monitored by histological analysis, expression of wnt/catenin target genes; measurement of proliferation in stem cell compartments; and the like. For example, inhibition of wnt may result in crypt loss followed by villus blunting and fusion and loss of mucosal integrity. Genes expressed in the gastrointestinal tract that are controlled by wnt/β-catenin include CD44, and EphB2. Antibodies specific for these proteins are commercially available. Analysis of proliferation may utilize staining for Ki67, which is a nuclear protein expressed in proliferating cells during late G1-, S-, M-, and G2-phases of the cell cycle, while cells in the G0 (quiescent) phase are negative.

For screening purposes one may utilize in vitro assays for wnt biological activity, e.g. stabilization of β-catenin, promoting growth of stem cells, etc. Assays for biological activity of Wnt include stabilization of β-catenin, which can be measured, for example, by serial dilutions of the Wnt composition. An exemplary assay for Wnt biological activity contacts a Wnt composition in the presence of a candidate inhibitor or activator with cells, e.g. mouse L cells. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

Cytoreductive therapy: Cytoreductive therapy, as used herein, includes radiotherapy and chemotherapy. Agents that act to reduce cellular proliferation are known in the art and widely used. Chemotherapy drugs that kill cancer cells only when they are dividing are termed cell-cycle specific. These drugs include agents that act in S-phase, including topoisomerase inhibitors and anti-metabolites.

Toposiomerase inhibitors are drugs that interfere with the action of topoisomerase enzymes (topoisomerase I and II). During the process of chemo treatments, topoisomerase enzymes control the manipulation of the structure of DNA necessary for replication, and are thus cell cycle specific. Examples of topoisomerase I inhibitors include the camptothecan analogs listed above, irinotecan and topotecan. Examples of topoisomerase II inhibitors include amsacrine, etoposide, etoposide phosphate, and teniposide.

Antimetabolites are usually analogs of normal metabolic substrates, often interfering with processes involved in chromosomal replication. They attack cells at very specific phases in the cycle. Antimetabolites include folic acid antagonists, e.g. methotrexate; pyrimidine antagonist, e.g. 5-fluorouracil, foxuridine, cytarabine, capecitabine, and gemcitabine; purine antagonist, e.g. 6-mercaptopurine and 6-thioguanine; adenosine deaminase inhibitor, e.g. cladribine, fludarabine, nelarabine and pentostatin; and the like.

Plant alkaloids are derived from certain types of plants. The vinca alkaloids are made from the periwinkle plant (*Catharanthus rosea*). The taxanes are made from the bark of the Pacific Yew tree (taxus). The vinca alkaloids and taxanes are also known as antimicrotubule agents. The podophyllotoxins are derived from the May apple plant. Camptothecan analogs are derived from the Asian "Happy Tree" (*Camptotheca acuminata*). Podophyllotoxins and camptothecan analogs are also classified as topoisomerase inhibitors. The plant alkaloids are generally cell-cycle specific.

Examples of these agents include vinca alkaloids, e.g. vincristine, vinblastine and vinorelbine; taxanes, e.g. paclitaxel and docetaxel; podophyllotoxins, e.g. etoposide and tenisopide; and camptothecan analogs, e.g. irinotecan and topotecan.

Radiotherapy includes exposure to radiation, e.g. ionizing radiation, UV radiation, as known in the art. A dose of ionizing radiation may range from at least about 2 Gy to not more than about 10 Gy. A suitable dose of ultraviolet radiation might range from at least about 5 $J/m^2$ to not more than about 50 $J/m^2$, usually about 10 $J/m^2$.

Pharmaceutical Formulations: The wnt inhibitor, and the anti-proliferative agent may be incorporated into a variety of formulations for therapeutic administration. The wnt inhibitor, and the anti-proliferative agent can be delivered simultaneously, or within a short period of time, by the same or by different routes. In certain embodiments, the wnt inhibitor is administered at least one, at least two at least 3 or more days prior to initiation of chemotherapy. Also included are formulations of wnt, or other agents that specifically block the inhibitor for use in chasing the inhibitor, following treatment with an anti-proliferative drug.

The active agents may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally.

Therapeutic Methods

Delivery of Wnt Inhibitor

In pharmaceutical dosage forms, the wnt inhibitor and/or other compounds may be administered in the form of their pharmaceutically acceptable salts, or they may also be used alone or in appropriate association, as well as in combination with other pharmaceutically active compounds. The agents may be combined to provide a cocktail of activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations comprise engineered polymer microspheres made of biologically erodible polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71(3):307-18.

In another embodiment, a microorganism, for example a virus, such as adenovirus, lentivirus, adeno-associated virus, etc.; bacterial cell; yeast cell, etc., capable of producing a wnt inhibitor polypeptide is administered to a patient. Such a culture may be formulated as an enteric capsule; for example, see U.S. Pat. No. 6,008,027, incorporated herein by reference. Alternatively, microorganisms stable to stomach acidity can be administered in a capsule, or admixed with food preparations. Alternatively, viral vectors may be administered systemically, e.g. by iv delivery.

Other formulations of interest include formulations of DNA encoding agents of interest, so as to target intestinal cells for genetic modification. For example, see U.S. Pat. No. 6,258,789, herein incorporated by reference, which discloses the genetic alteration of intestinal epithelial cells.

Formulations are typically provided in a unit dosage form, where the term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Those of skill will readily appreciate that dose levels can vary as a function of the specific enzyme, the severity of the symptoms and the susceptibility of the subject to side effects. Some of the agents will be more potent than others. Preferred dosages for a given agent are readily determinable by those of skill in the art by a variety of means. A preferred means is to measure the physiological potency of a given compound.

The dosage regimen for increasing normal cell survival following chemotherapy is based on a variety of factors, including the type of cancer, the age, weight, sex, medical condition of the individual, the severity of the condition, the route of administration, and the particular compound employed. Thus, the dosage regimen may vary widely, but can be determined routinely by a physician using standard methods. Dosage levels of the order of between 0.1 ng/kg and 10 mg/kg body weight of the active agents per body weight are useful for all methods of use disclosed herein.

The methods find use in conditions where an antiproliferative agent is administered, and where it is desirable to spare normal stem cells that are otherwise killed by the anti-proliferative agent. The patient is typically mammalian, and may be primate, including human, may be used for veterinary purposes, e.g. canines, felines, ovines, equines, etc., or may be used in animal models for disease, e.g. murines, including rats and mice, lagomorphs, and the like. Conditions treated by anti-proliferative agents include treatment of autoimmune disease; antimicrobial treatments, particularly treatment of parasites and other eukaryotic microbes; and particularly, for the treatment of cancers. The treatment of cancer with anti-proliferative agents is well-known in the art, and need not be repeated herein.

In the methods of the invention, an effective dose of a wnt inhibitor will render normally wnt responsive cells, e.g. gut epithelial cells, hematopoietic stem cells, bone marrow mesenchymal stem cells, neural stem cells, etc., quiescent for a period of time. Typically a dose will be effective for at least the period of time during which an anti-proliferative agent is being administered, usually at least about 12 hours, more usually at least about 1 day, and frequently for a period of about 2 days, about 3 days, or more, usually not more than about 2 weeks, more usually not more than about 7 days. The therapy is administered for 1 to 6 times per day at dosages as described below. In all of these embodiments, the protective compounds of the invention can be administered prior to, simultaneously with, or subsequent to chemotherapeutic exposure. For example the compounds may be administered about 3 days prior, 2 days prior, or 1 day prior to chemotherapy.

Optionally, after a period of time that is effective for action of the anti-proliferative agent, a dose of wnt polypeptide or wnt mimetic is administered to the patient, in a dose that competitively blocks the wnt inhibitor, allowing normal cell proliferation to resume. The methods may be combined with various supportive therapy used in the art, e.g. administration of erythropoietin, GM-CSF, G-CSF, etc., usually after resumption of normal cell proliferation; transfer of blood cells including stem and progenitor cells, red cells, etc.

In another embodiment of the invention, a subject undergoes repeated cycles of treatment according to the method of this invention. Preferably, a subsequent treatment cycle commences only after the administration of the compounds of the invention has been terminated and the subject's blood cell counts (e.g., white blood cell count) have returned to a therapeutically acceptable level, permitting the repeated chemotherapy.

Kits are provided for increasing stem cell survival following chemotherapy, wherein the kits comprise an effective amount of the protective agent for increasing stem cell survival following chemotherapy, and instructions for using the amount effective of active agent as a therapeutic. Optionally, the kit further comprises a wnt or other quenching molecule in composition suitable for administering to chase the protecting agent at the conclusion of chemotherapy. Quenching molecules are any agent that specifically inactivates the protecting agent, either competitively or non-competitively.

In a preferred embodiment, the kit further comprises a pharmaceutically acceptable carrier, such as those adjuvants described above. In another preferred embodiment, the kit further comprises a means for delivery of the active agent to a patient. Such devices include, but are not limited to syringes, matrical or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery may either contain the effective amount of the active agents, or may be separate from the compounds, which are then applied to the means for delivery at the time of use.

In one embodiment, the kit comprises a protective agent that blocks extracellular wnt signaling and instructions for administering to a patient said protective agent in an amount effective to detectably inhibit the binding of extracellular wnt to frizzled present on the surface of said stem cell as a therapeutic. The kit may further comprise a pharmaceutically acceptable carrier with which to admix said protective agent; and may comprise a means for delivery of the protective agent to a patient. The kit may further comprise a chemotherapeutic agent and instructions for administering to a patient said chemotherapeutic agent in conjunction with said protective agent in a therapeutic regime. The kit may further comprise a wnt polypeptide or a wnt mimetic and instructions for administering to a patient said wnt polypeptide or said wnt mimetic in an amount effective to competitively blocks the protective agent and allow normal stem cell proliferation to resume in a therapeutic regime.

EXPERIMENTAL

Example 1

Assessment of Stem Cell Dependence on Wnt Signaling

HSCs in their normal microenvironment activate a LEF-1/TCF reporter, which indicates that HSCs respond to Wnt signaling in vivo. To demonstrate the physiological significance of this pathway for HSC proliferation, it is shown herein that the ectopic expression of axin or a frizzled ligand-binding domain, both of which are inhibitors of the Wnt signaling pathway, led to inhibition of HSC growth in vitro and reduced reconstitution in vivo. Furthermore, activation of Wnt signaling in HSCs induces increased expression of HoxB4 and Notch1, genes previously implicated in self-renewal of HSCs. It can be concluded that the Wnt signaling pathway is critical for normal HSC homeostasis in vitro and in vivo.

β-catenin expression leads to self-renewal of HSCs in vitro. We first determined the effects of activating downstream components of the Wnt pathway on HSC function. We activated Wnt signaling in HSCs sorted via fluorescence-activated cell sorting (FACS) (c-Kit$^+$ Thy-1.1$^{lo}$ Lin$^{-/lo}$ Sca-1$^+$ (KTLS) cells) by retrovirally transducing them with constitutively active β-catenin. Successful transduction of HSCs with retroviruses requires induction of cell cycle entry through the use of multiple growth factors, which can promote differentiation of stem cells in vitro. To minimize the pro-differentiation stimuli encountered by HSCs during infection before experiments of interest, we used HSCs from H2K-BCL-2 transgenic mice, which proliferate in the presence of steel factor (SLF) alone. Sorted BCL-2 transgenic HSCs were infected with retroviruses encoding either β-catenin-IRES-GFP (β-catenin, internal ribosome entry site and green fluorescent protein) or IRES-GFP alone, and GFP expression was detected in 45-55% of HSCs, which persisted for the entire in vitro culture period. GFP-positive (GFP$^+$) HSCs were sorted to determine growth kinetics in vitro and the ability to +reconstitute the immune system in vivo.

Short-term growth characteristics of HSCs expressing β-catenin or control vector were determined by cell cycle analysis. In FIG. 1A, whereas 34% of the HSCs infected with control vector were in S/G2/M phases of the cell cycle, 58% of the HSCs expressing activated β-catenin were in the same phases of the cell cycle. To determine whether activated Wnt signaling increased long-term growth, HSCs expressing β-catenin were grown in vitro in serum-free medium in the presence or absence of growth factors. Medium containing limiting amounts of SLF allowed the growth of β-catenin-transduced HSCs consistently for at least 8 weeks (FIG. 1b). During this period the GFP$^+$ cells underwent eight to nine population doublings to generate at least 100 times the number of input cells. In contrast, HSCs infected with control vector showed minimal growth beyond a two-week period. On complete withdrawal of SLF during long-term culture, β-catenin-infected HSCs grew for at least 4 weeks, and in some experiments could be maintained and passaged for as long as 1-2 months. In contrast the control transduced HSCs did not survive beyond 48 h.

To determine whether growth in response to activated β-catenin was accompanied by differentiation, the morphological characteristics of these cells were analyzed at the end of a two-week period. This time point was chosen to be able to compare the differentiation status of control and β-catenin-transduced HSCs, as the lifespan of HSCs transduced with control vector was limited. Cells infected with control vector were found to have a myelomonocytic appearance. In contrast, 65-75% of the β-catenin-transduced HSCs had a high nuclear to cytoplasm ratio (FIG. 1C). Consistent with this, although most (75-80%) of the HSCs infected with control vector were positive for lineage markers (FIG. 1D), only 5-10% of cells infected with β-catenin expressed high levels of lineage markers (predominantly Mac-1, an integrin expressed on fetal HSCs and regenerating HSCs). In fact, 60% of HSCs infected with β-catenin were lineage-negative and expressed high levels of c-Kit and Sca-1 and almost half of these also expressed low levels of Thy-1.1. Thus, at least 30% of the cells in β-catenin-transduced cultures had retained the phenotype of HSCs; that is, c-Kit$^+$ Thy1.1$^{lo}$ Lin$^-$ Sca-1$^+$ (KTLS cells). This indicated that the expression of activated β-catenin maintained hematopoietic stem cells in an immature state, while simultaneously allowing these cells to proliferate, thus expanding the HSC pool 20- to 48-fold on the basis of the total numbers of cells generated.

Figure 5:
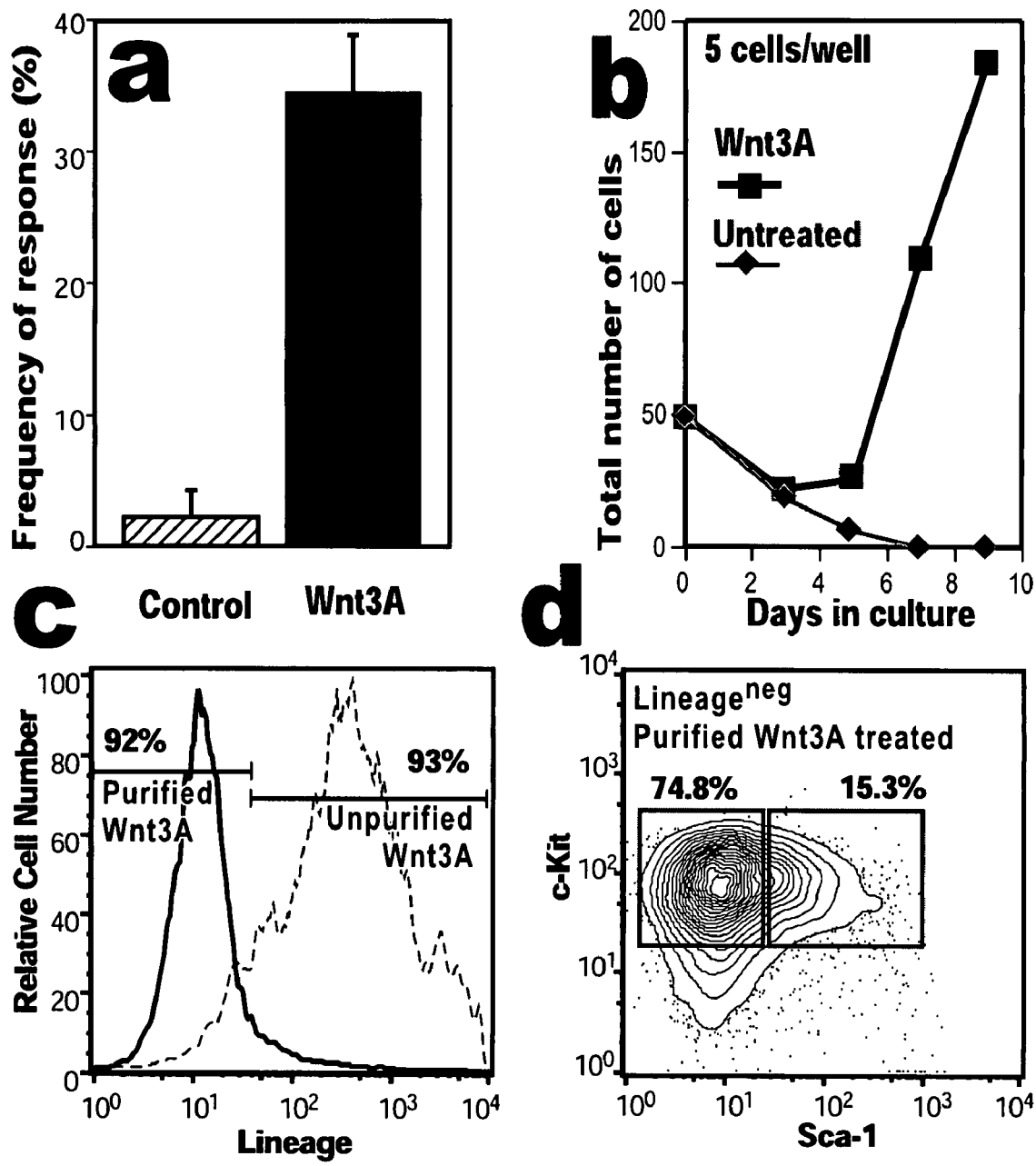
FIGS. 5A-5D. Wild Type HSCs proliferate to purified Wnt3A. Purified wild type mouse bone marrow HSCs were sorted by FACS and plated at 5 or 10 cells/well into 60 well Terasaki plates. Cells were incubated in X-vivo 15 (Bio Whittaker), 10% FBS, 5×10⁻⁵M 2-Mercaptoethanol, and 1×10⁻⁴ M random methylated beta-cyclodextrin (CTD, Inc.) in the presence of either purified Wnt3A (at approx. 100 ng/ml) plus SLF (10 ng/ml) or SLF (10 ng/ml) alone, as a control. (SLF dose required ranged from 7.5 ng/ml-100 ng/ml depending on mouse strain used). Cell growth was monitored over a period of 7-9 days in culture, and is shown as total cell response (A) and the average frequency of responding wells (B) representative of over 9 independent experiments. To determine phenotypic characteristics, cells were plated in bulk (3500 cells) in 96 well plates and incubated in the presence of purified or unpurified Wnt3A. After seven days in culture, a majority of cells treated with purified Wnt3A (at 100 ng/ml) were negative for lineage markers (solid line) while a majority treated with unpurified Wnt3A (calculated to be at 200 ng/ml in the medium) strongly upregulated Lineage markers (dashed line) (C). FACS analysis of the purified Wnt3A treated cells demonstrated that the lineage negative population was distributed into c-Kit⁺ and Sca-1⁺ HSCs and c-kit⁺ and Sca-1⁻ myeloid progenitors (D).
Figure 6:
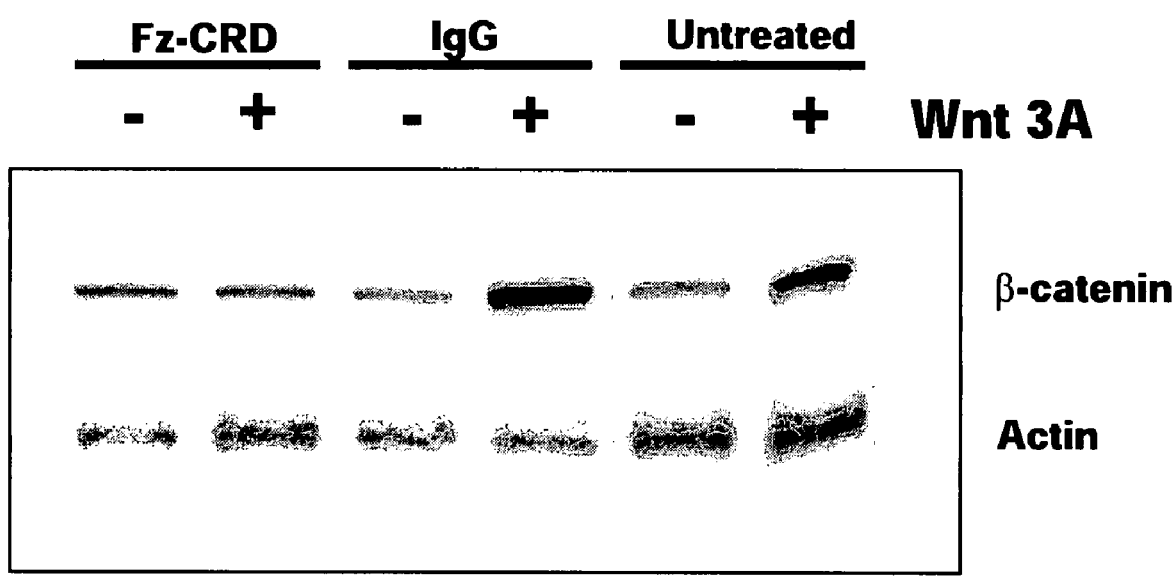
FIG. 6. IgG-CRD inhibits Wnt mediated beta-catenin stabilization. 50,000 L cells were plated in a 24-well plate and treated with Wnt3A alone or Wnt3A in the presence of IgG-CRD (1:1) or control IgG (1:1). 12 hours after stimulation, cells were harvested and lysed (0.5% NP-40+20 mM Tris-pH8.0+170 mM NaCl, 1 mM EDTA-pH8.0+1 mM DTT+0.2 mM $Na_3VO_4$+protease inhibitors) for 15 min. on ice. Soluble protein lysates were separated by SDS-PAGE and transferred to PVDF. Western blots were probed with anti-β-catenin (BD Transduction Laboratories) and anti-actin (Sigma) antibodies.
Figure 7:
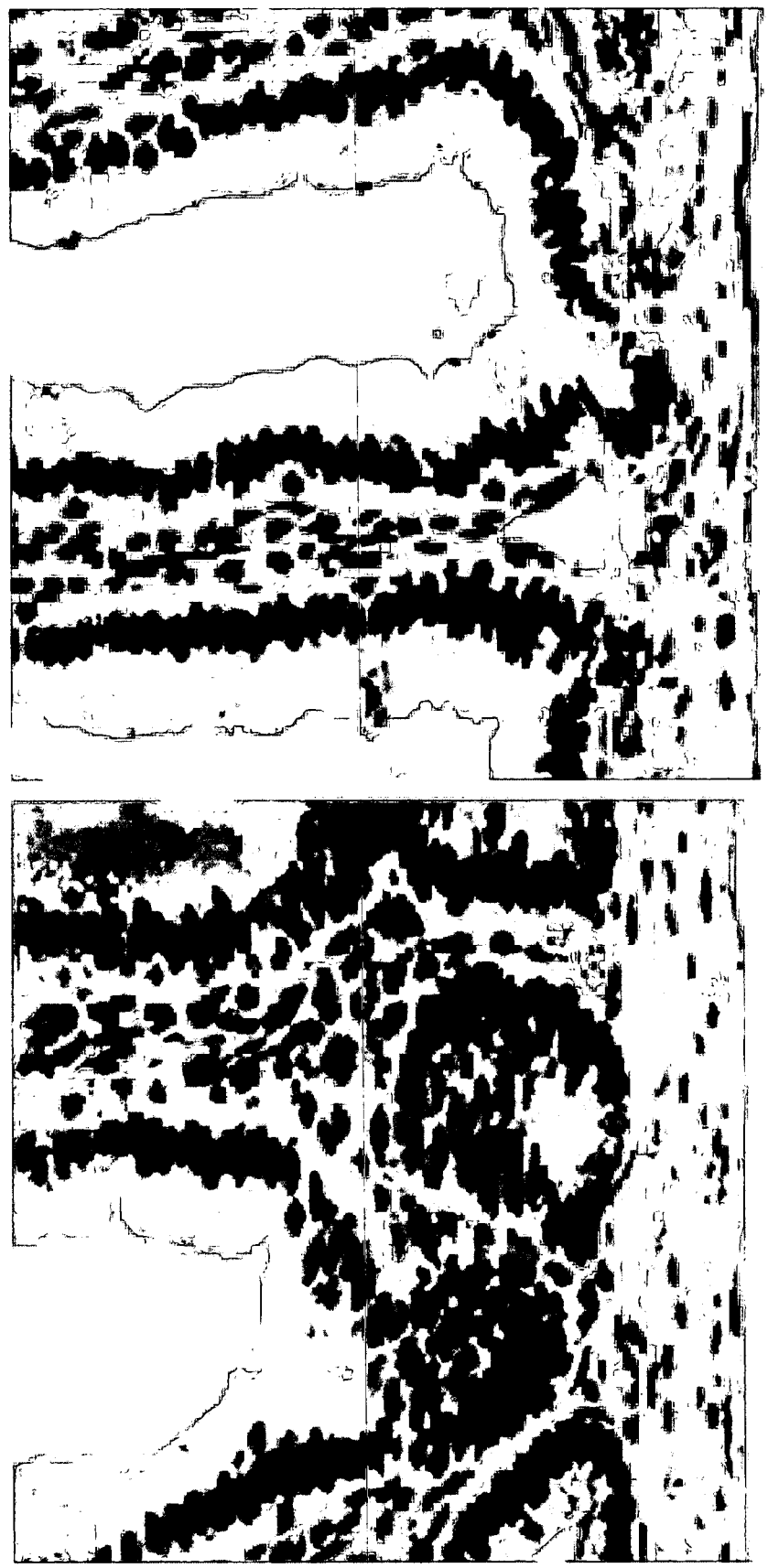
FIG. 7 depicts the effect of blocking Wnt signaling in the intestines.
Figure 8:
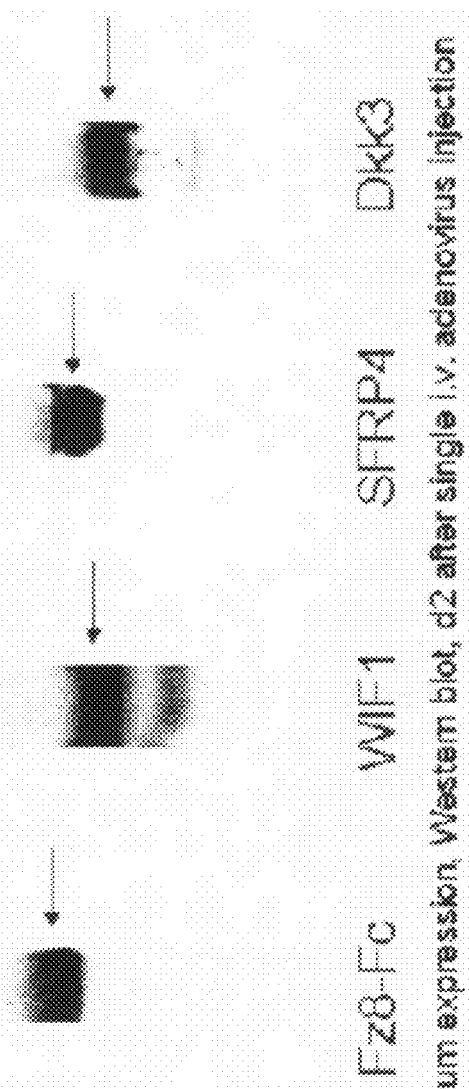
FIG. 8 depicts a schematic of adenoviruses encoding different classes of secreted Wnt inhibitors, and expression of the inhibitors following iv injection into a mouse.
Figure 8:
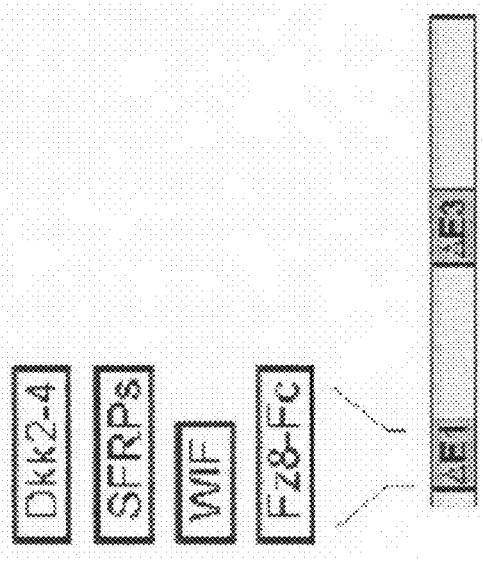

Without wishing to be bound by theory, we believe that the expansion of HSCs owing to activated β-catenin reflects upstream Wnt signals. It was demonstrated that purified Wnt3a causes self-renewal in both BCL-2 transgenic and wild-type HSCs (FIGS. 5-6). Specifically, singly plated HSCs generate six-fold or more numbers of progeny in the presence of Wnt3a compared with control conditions. These daughter cells not only maintain an immature phenotype, but also display a 5- to 50-fold expansion of HSC function as determined by transplantation analysis of the progeny of single HSCs after expansion in vitro.

Based on the numbers of cells seeded after beta-catenin infection (10,000) and the increase in numbers over an eight week period (960,000), expression of activated beta-catenin in HSC typically led to at least a 20- to 48-fold expansion of cells with a stem cell phenotype (30% of 960,000=288,000, an underestimate as at least some of the 10,000 initial cells probably neither survive nor respond).

The data using limited dilution transplants allowed us to conclude that significant functional expansion of HSCs occurs in the presence of beta-catenin. Since all of the mice transplanted with 125 beta-catenin transduced HSCs were successfully reconstituted, we estimate based on efficiency of engraftment (10% KTLS cells can reconstitute the marrow) that each transplant must have contained at least 10 HSCs/125 cells (~10%) and likely much more since the reconstitution observed was at a high level. In a representative experiment carried out for 1 week we observed that 6,000 HSCs plated result in 48,000 cells. Based on the fact that 10% of this expanded population retain HSC activity (4,800), and that 10% of the plated HSCs would read out functionally (600) this suggests at least an 8-fold and up to an 80-fold (if 100% of cultured cells retained HSC activity) expansion of HSC function in the presence of activated beta-catenin. However, based on the fact that there is significant cell death initially, as well as the fact that cycling cells are far more inefficient at transplanting in vivo (~1/50 cells or 2% read out functionally), the lower estimate of 8-fold is very likely an underestimate of the expansion that actually occurred. Based on the proliferation observed in cultures carried out for a longer period of time (2 months, FIG. 1), we estimate that a 96-960 fold functional expansion of HSCs occurred in long term cultures.

Wnt3A induces proliferation of wild type HSCs in vitro. Purified Wnt protein can regulate HSC self-renewal in the same manner as β-catenin in BCL-2 transgenic HSCs. To ensure that this response was not dependent on BCL-2 overexpression, we specifically tested whether wild type HSCs respond in a similar manner to purified Wnt3A as well. Over a period of days, HSCs plated at 1-20 cells per well, responded extremely robustly to Wnt3A in contrast to control conditions (e.g. 184 cells versus 0 when plated at 5 cells/well) (FIG. 5). The average frequency of cells that responded to Wnt3A over 3 independent experiments was 17-fold more than the proliferation to control conditions (limiting dose of SLF) when plated at 10 cells/well. These data are representative of over 9 independent experiments utilizing different numbers of input cells (1-20 cells/well). Furthermore, the phenotypic characteristics of HSCs treated with purified or unpurified Wnt3A were dramatically different. After 7 days in culture, a majority of HSCs treated with purified Wnt3A were negative for lineage markers (solid line) while a majority treated with unpurified Wnt3A strongly upregulated lineage markers (dashed line) (C). Furthermore, a significant fraction of the lineage negative population expressed c-Kit and Sca-1 consistent with a HSC phenotype (D).

To test whether the cells treated with purified Wnt3A underwent self-renewal functionally, purified HSCs were plated as 1 cell or as 10 cells, treated with Wnt3A and each well containing proliferating cells transplanted individually into lethally irradiated recipient mice along with 300,000 Sca-1$^-$ Bone Marrow cells (A). Analysis of peripheral blood (PB) from each transplanted mouse revealed multilineage reconstitution indicative of a HSC readout (B). Since the empirically observed frequency of reconstitution of resting HSCs is ~10% and of cycling HSCs ~2%, the observed frequency of reconstitution of 100% for 1 plated cells is consistent with Wnt3A inducing a 10- to 50-fold increase in HSC activity, a range similar to that seen with BCL-2 transgenic HSCs. Additionally in independent experiments wells plated with 10 cells as well as those plated with 5 cells also displayed 100% reconstitution efficiency consistent with increased self-renewal of cycling HSCs in response to Wnt3A. The facts that HSCs proliferated in response to Wnt3A in vitro, the increased maintenance of stem cell phenotypic characteristics and the functional increase in self-renewal occurs in both BCL-2 transgenic and in wild type mice, demonstrates that ectopic expression of BCL-2 is not essential for the responsiveness of HSCs to Wnt3A.

Figure 2:
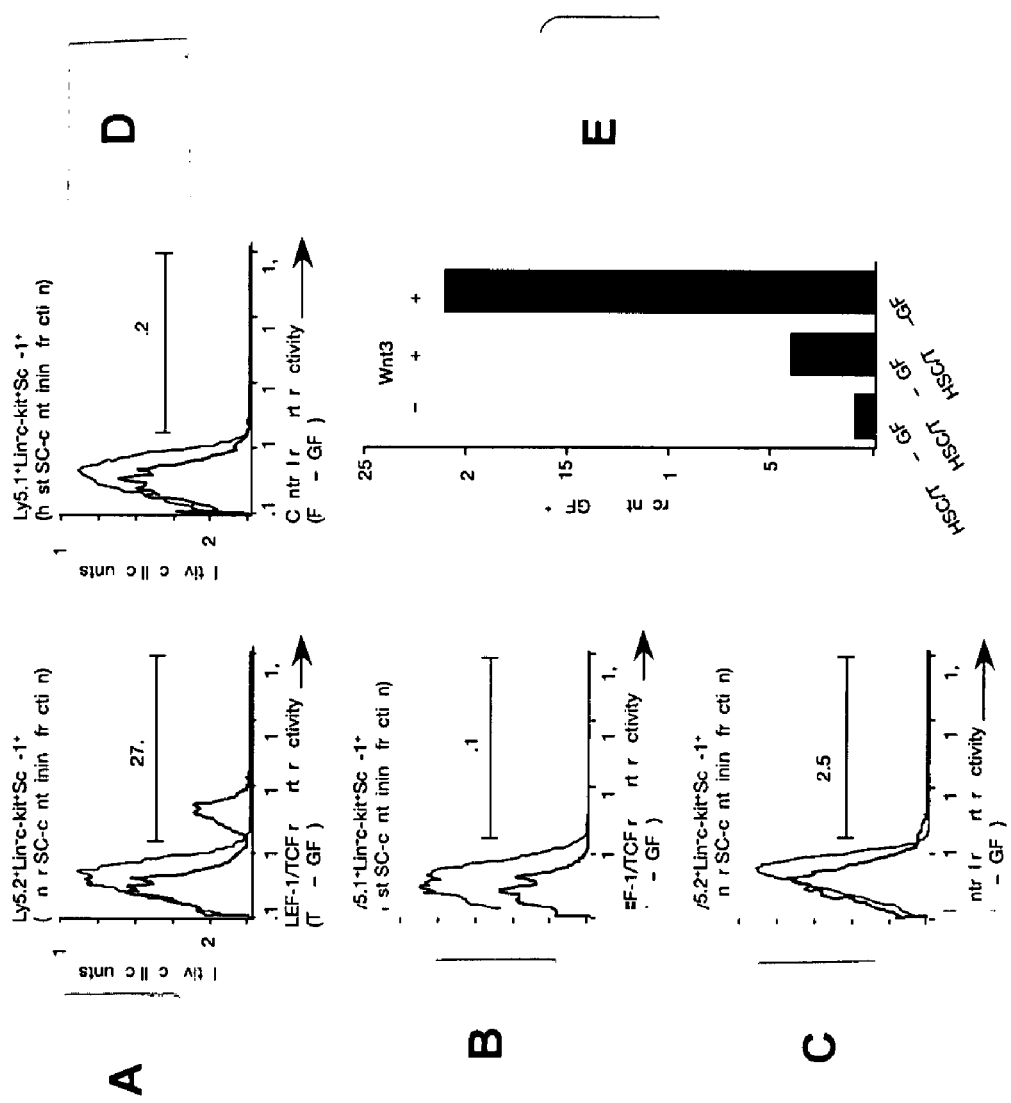
FIGS. 2A-2E. HSCs respond to Wnt signaling in native bone marrow microenvironment. HSCs were infected with a lentiviral reporter containing either LEF-1/TCF binding sites linked to destabilized GFP (TOP-dGFP), or mutated LEF-1/TCF binding sites linked to destabilized GFP (FOP-dGFP). Infected HSCs were transplanted into three lethally irradiated recipient mice, and analyzed after 14 weeks. The data shown represent two independent experiments. a, b, GFP expression is shown in donor-derived (a) or host-derived (b) HSCs. c, d, Donor-derived HSCs carrying mutated LEF-1/TCF reporter (c) as well as the recipient mouse HSCs (d) are GFP negative. Expression of GFP in donor-derived Lin⁻ c-Kit⁺ Sca-1⁻ cells (non-HSCs) is shown by thin lines (a-d). e, HSCs infected with TOP-dGFP or TOP-GFP (a non-destabilized GFP) were stimulated in vitro with control medium or with 100 ng ml⁻¹ Wnt3a, and the extent of GFP expression measured.

HSCs in vivo normally signal through LEF-1/TCF elements. To determine whether the Wnt signaling pathway is physiologically relevant to HSCs, we tested whether HSCs in vivo use signals associated with the Wnt/$\beta$-catenin pathway. HSCs were infected with LEF-1/TCF reporter driving expression of destabilized GFP (TOP-dGFP) or with control reporter with mutated LEF-1/TCF binding sites (FOP-dGFP), and then transplanted into lethally irradiated mice. Recipient bone marrow was examined after 14 weeks to determine whether donor HSCs demonstrated reporter activity. In the example shown, donor-derived HSCs infected with TOP-dGFP expressed GFP in 28% of the cells (FIG. 2; range observed 4-28%, mean 11.8%), whereas HSCs from the recipient mouse were negative for GFP (range observed 2.3-3.2%, mean 2.7%). Moreover, HSCs transduced with the control reporter did not express GFP significantly, demonstrating that functional LEF-1/TCF binding sites were required for HSC expression of GFP (FIG. 2C). In all cases, no reporter activity was observed in the non-HSC myeloid progenitor fraction (FIG. 2, thin line).

As a control, we also tested whether the TOP-dGFP reporter was turned on in response to Wnt3a-mediated signaling in HSCs in vitro. Thus, HSCs transduced with either TOP-dGFP or FOP-dGFP were stimulated with Wnt3a, and the extent of GFP expression was monitored. As shown in FIG. 2E, Wnt3a-treated HSCs showed significant reporter activity, demonstrating that the reporter is turned on in response to Wnt stimulus, but not in control conditions. Increased reporter activity was observed when the reporter construct driving non-destabilized GFP was used. These data demonstrate that HSCs in their normal microenvironment respond to endogenous Wnt signaling during self-renewal and/or stimulation into cell cycle, and also support the interpretation that the Wnt3a stimulus that caused increased self-renewal signals through the canonical Wnt pathway.

Figure 3:
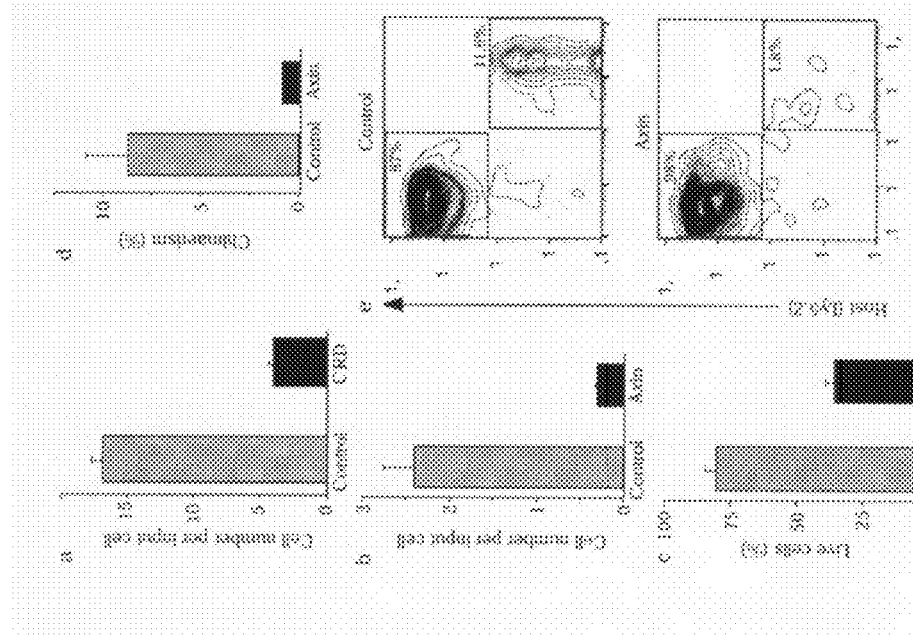
FIGS. 3A-3E. Inhibition of Wnt signaling reduces growth of HSCs in vitro and inhibits reconstitution in vivo. a, HSCs (20 cells per well) were cultured for 60 h in medium containing mitogenic factors and either IgG-CRD or control IgG. b, HSCs were infected with virus encoding axin-IRES-GFP or GFP alone. Growth of infected HSCs in the presence of mitogenic factors was monitored over 60 h. c, The number of live cells was determined by propidium iodide staining. d, e, The development of HSCs in vivo was determined by injecting 1,000 control or axin-infected cells per mouse into groups of four lethally irradiated, allelically marked (Ly5.2) host mice along with 300,000 competing syngeneic bone marrow cells. Cells were isolated from peripheral blood and analyzed by flow cytometry after >10 weeks. Donor-derived (Ly5.1⁺) cells were monitored in the peripheral blood of hosts; analysis from a representative recipient and average reconstitution is shown.

HSCs require intact Wnt signaling. To test whether Wnt signaling is required for normal HSC growth, we used a soluble form of the frizzled cysteine-rich domain (CRD) that inhibits the binding of Wnt proteins to the frizzled receptor (FIG. 6). Wild-type HSCs were incubated with growth factors in the presence of IgG-CRD domain fusion protein or control IgG, and cell proliferation was monitored. The presence of the CRD domain inhibited growth of HSCs fourfold compared with control conditions (FIG. 3A). This inhibition provides direct evidence of a Wnt signal modulating HSC survival and proliferation, as soluble CRD acts at the level of Wnt binding the frizzled molecules. Because only HSCs were present, the Wnt signal is probably derived from some or all of the HSCs in the cultures, and is required despite the presence of multiple other growth factors. These results can be interpreted to mean that all HSC mitoses are the result of Wnt signaling, even if the primary signals are not Wnt.

We also inhibited Wnt signaling through an independent inhibitor by ectopically expressing axin in HSCs. Axin increases $\beta$-catenin degradation and acts as an intracellular inhibitor of Wnt signaling. Live axin-infected wild-type HSCs were re-sorted 48 h after infection and plated in limiting numbers to assay growth in response to a combination of growth factors. Although control-infected cells proliferated 2.3-fold over 60 h, axin-infected cells showed a sevenfold reduction in the total growth response (FIG. 3b). Axin had an inhibitory effect on growth of BCL-2 transgenic HSCs as well, which suggests that expression of BCL-2 cannot protect cells from loss of Wnt signaling. To determine whether axin expression had an effect on cell survival, GFP$^+$ cells were analyzed at the end of the infection period using propidium iodide exclusion. Whereas 80% of the control-infected cells were negative for propidium iodide, only 38% of axin-infected HSCs were negative for propidium iodide, indicating that axin expression has significant effect on cell survival by blocking $\beta$-catenin function.

To determine whether Wnt signaling is required for hematopoietic stem cell responses in vivo, we injected axin- or control-transduced viable HSCs into lethally irradiated mice and analyzed the level of reconstitution after 10 weeks. Mice transplanted with control-infected HSCs displayed on average sevenfold greater chimerism (reconstitution range 5-11.6%) than mice transplanted with axin-infected HSCs (reconstitution range 0-1.8%) (FIG. 3E). A representative example of contribution from axin- or vector-infected HSCs in transplanted mice is shown in FIG. 3d. These data show that inhibition of the Wnt pathway reduces reconstitution, suggesting that Wnt signaling is required for normal development of HSCs in vivo. This finding, together with the finding that HSCs respond to Wnt signaling in vivo (FIG. 2), indicates that Wnt/$\beta$-catenin signaling is an important physiological mediator of HSC-derived hematopoiesis.

$\beta$-catenin upregulates HoxB4 and Notch1 in HSCs. We wished to determine whether Wnt signaling might be regulating HSC self-renewal by upregulating genes previously implicated in HSC self-renewal. To this end we tested upregulation of HoxB4 and Notch1. By using real-time polymerase chain reaction (PCR) analysis on HSCs infected with either $\beta$-catenin or control vector, we found that HoxB4 was upregulated an average of 3.5-fold and Notch1 was upregulated 2.5-fold (FIG. 4a). In contrast, GADPH expression was not differentially regulated as a consequence of $\beta$-catenin expression, and was used as a control (FIG. 5b). These data show that genes so far identified as regulators of HSC self-renewal may be related and perhaps act in a molecular hierarchy.

The above data show that components of the Wnt signaling pathway can induce proliferation of purified KTLS bone marrow HSCs while significantly inhibiting their differentiation, thereby resulting in functional self-renewal. Expression of $\beta$-catenin in HSCs results in increased growth with significantly reduced differentiation in vitro for a period of at least many weeks. HSCs transduced with $\beta$-catenin give rise to sustained reconstitution of myeloid and lymphoid lineages in vivo, when transplanted in limiting numbers. Wnt signaling is required for the growth response of normal HSCs to other cytokines, as overexpression of axin leads to reduced stem cell growth both in vitro and in vivo. Furthermore, the inhibition of HSC growth with frizzled-CRD and the finding that Wnt3a causes expansion of HSCs supports the interpretation that the effects of $\beta$-catenin and axin reflect upstream Wnt activity. Finally, studies with HSCs containing a LEF-1/TCF reporter indicate that HSCs in vivo respond to endogenous Wnt stimulation. The expression of a number of Wnt proteins in the bone marrow and frizzled receptors in bone-marrow-derived progenitors and HSCs supports this possibility.

Most growth factors that act on HSCs in culture induce no or limited expansion or are unable to prevent differentiation. Thus, one of the most notable findings of our work is the induction of proliferation and the prevention of HSC differentiation by the Wnt signaling pathway. Other signals that increase proliferation of HSCs include Notch and sonic hedgehog. Moreover, the cyclin-dependent kinase inhibitor $p21^{Cip1/Waf1}$ and the transcription factor HoxB4 have been shown to be involved in regulating self-renewal of HSCs. Notably, Wnt signaling has been shown to interact with many of these pathways in a variety of organisms, and the above data show that both HoxB4 and Notch1 are upregulated in response to Wnt signaling in HSCs.

These findings have important implications for human hematopoietic cell transplantation. Soluble Wnt3a protein induces proliferation of highly purified human bone marrow HSCs in the absence of any other growth factor. Induction of HSC growth by Wnt signaling may allow in vitro expansion of a patient's own or an allogenic donor's HSCs, and could provide an increased source of cells for future transplantation. Conversely, by inhibiting Wnt signaling, HSC can be arrested in a quiescent stage.

Materials and Methods

Mice. C57Bl/Ka Ly5.1, Thy-1.1 (wild-type and BCL-2), C57Bl/Ka Ly5.2, Thy-1.1, and AKR/J mice were used at 6-10 weeks of age. Mice were bred and maintained on acidified water in the animal care facility at Stanford and Duke University Medical Centers.

HSC isolation. We sorted HSCs from mouse bone marrow. All cell sorting and FACS analysis was carried out on a FACSVantage (Becton Dickinson) at the Stanford shared FACS facility and the Duke Cancer Center FACS facility. Cells were sorted and reanalyzed on the basis of expression of c-Kit, Sca-1, low levels of Thy-1.1, and low to negative levels of lineage markers (Lin).

Cell cycle analysis. Retrovirally transduced HSCs were collected from cultures and stained with Hoechst 3342 (Molecular Probes) at 37° C. for 45 min in Hoechst medium. Cells were then washed and analyzed by Flow cytometry to determine the cell cycle profile of $GFP^+$ cells.

Viral production and infection. Virus was produced by triple transfection of 293T cells with murine stem cell virus constructs along with gag-pol and vesicular stomatitis virus G glycoprotein constructs. Viral supernatant was collected for three days and concentrated 100-fold by ultracentrifugation at 50,000 g. For viral infection, 10,000 HSCs were sorted into wells of a 96-well plate and cultured overnight in the presence of SLF (30 ng $ml^{-1}$) for BCL-2 transgenic HSCs, or SLF (30 ng $ml^{-1}$) plus TPO (30 ng $ml^{-1}$) for wild-type HSCs. After 12 h, concentrated retroviral supernatant was added to the cells at a 1:1 ratio. Cells were then incubated at 32° C. for 12 h and 37 C for 36 h before $GFP^+$ cells were sorted for in vitro and in vivo assays. Lentiviruses used were produced as previously described. Briefly, 293T cells were transfected with the transfer vector plasmid, the VSV-G envelope-encoding plasmid pMD.G, and the packaging plasmid CMVΔR8.74. The supernatant was collected and concentrated by ultracentrifugation. All cytokines were purchased from R&D systems.

In vitro HSC proliferation assays. Freshly purified or virally transduced HSCs were plated at 1 to 20 cells per well in Terasaki plates. Cells were sorted into wells containing serum-free medium (X-vivo15, BioWhittaker) supplemented with $5 \times 10^{-5}$ M 2-mercaptoethanol and the indicated growth factors. Proliferation was monitored by counting the number of cells in each well at defined intervals. For longer-term cultures, transduced HSCs were plated in 96-well plates in the absence or presence of SLF (1 ng $ml^{-1}$), and the number of cells generated was monitored by cell counting at defined intervals. For inhibition of growth by CRD or axin, cells were cultured in the presence of mitogenic factors (SLF (30 ng $ml^{-1}$), Flt-3L (30 ng $ml^{-1}$), interleukin-6 (10 ng $ml^{-1}$)).

In vivo analysis of HSC function. Virally transduced HSCs were cultured in vitro and injected retro-orbitally into groups of 4-6 congenic recipient mice irradiated with 9.5 Gy using a 200-kV X-ray machine, along with 300,000 rescuing host total bone marrow or Sca-1-depleted bone marrow cells. Host mice were given antibiotic water after irradiation. Transplanted mice were bled at regular periods to determine the percentage of the hematopoietic compartment contributed by donor cells. Donor and host cells were distinguished by allelic expression of CD45 (Ly5) or expression of the BCL-2 transgene.

Lentiviral reporter assays. The enhanced GFP (eGFP) or the d2-eGFP gene (destabilized, half-life of 2 h; Clontech) was cloned downstream of a LEF-1/TCF-responsive promoter, containing three LEF-1/TCF binding motifs and a TATA box. This cassette was then cloned into a self-inactivating lentiviral vector plasmid, and virus was produced as described above.

For in vivo assays, HSCs were transduced with reporter lentiviruses and cultured in X-Vivo15 with glutamate, $5 \times 10^{-5}$ M 2-mercaptoethanol, and a cocktail of cytokines including 10 ng $ml^{-1}$ interleukin-11, 10 ng $ml^{-1}$ TPO, 50 ng $ml^{-1}$ SCF, 50 ng $ml^{-1}$ Flt-3L. Cells were incubated at 37° C. for 6 h overnight and transplanted into lethally irradiated congenic recipients. Lethally irradiated mice received 500 transduced HSCs along with rescue bone marrow. For analysis, hematopoietic progenitor cells were analyzed for reporter activation 14-24 weeks after transplantation.

For in vitro assays, purified HSCs were sorted directly into medium (IMDM/10% FBS plus interleukin-11, TPO, SCF and Flt-3L, as above) and plated at 500-1,000 cells per well in 96-well plates. Individual wells were transduced with the appropriate lentiviral reporter and stimulated with or without purified Wnt3a (about 100 ng $ml^{-1}$). Cells were collected 5 days later, stained with propidium iodide to exclude non-viable cells, and analyzed for GFP expression.

Real-time PCR analysis. A total of 75,000 HSCs cultured in 96-well plates containing X-Vivo15, $5 \times 10^{-5}$ M 2-mercaptoethanol and 100 ng $ml^{-1}$ SLF were infected with either β-catenin or control lentiviruses. After two days in culture, transduced cells were isolated on the basis of GFP expression. RNA was prepared using Trizol (Invitrogen) and linearly amplified using a modified Eberwine synthesis. Each amplified RNA was converted to the first strand and analyzed for differential gene expression by real-time PCR. Complementary DNAs were mixed with FastStart Master SYBR Green polymerase mix (Roche), primers and real-time PCR was performed using a LightCycler (Roche).

Example 2

Analysis of Human Stem Cell Viability in an Animal Model

A SCID-hu animal model is set up for human bone marrow. The human HSC are tested after induction of quiescence for the presence of non-proliferating cells; and for the resumption of normal hematopoiesis after the quiescent period. The cells are then tested for resistance to killing by anti-proliferative agents that target proliferating cells.

Scid-hu bone marrow model. Human fetal femurs and tibias (1-2 cm) at 17-22 gestational week (g.w.), which are known to be active in hematopoiesis, are cut along a longitudinal axis so that bone cortex as well as intramedullary regions is exposed. These fragments are then surgically implanted subcutaneously into SCID mice. Homozygous CB-17 scid/scid mice are bred, treated with antibiotics as described (McCune et al., Science (1988) 241:1632), and used when 6-8 weeks old. Methoxyflurane anesthesia is applied during all operative procedures. Hematoxylin-eosin stained tissue sections are prepared from bone grafts 2 weeks and 8 weeks after implantation. The tissues are fixed in 20% formalin, decalcified with EDTA (1.7 mM) in HCl solution, paraffin embedded, and 4 μm sections are cut and stained with hematoxylin and eosin. Grafts are removed at varying intervals after implantation and analyzed for the presence of human hematopoietic activity.

The cell suspensions are prepared from implanted or normal bone marrow tissues, treated with 0.83% of ammonium chloride for 5-10 min at room temperature to lyse red blood cells, and washed with PBS. The cells are incubated with either biotinylated-MEM-43, biotinylated-Ly5.1, or biotinylated control antibodies for 45 min on ice, washed through a fetal bovine serum (FBS) cushion, and then stained with fluorescein conjugated (FITC-) avidin (Caltag Laboratories Inc.) for 45 min. Before flow cytometry, propidium iodide (PI) is added at final concentration of 10 μg/ml to gate out dead cells. Forward and side scattering patterns of the MEM-43 positive cells is obtained by four parameter flow cytometry using a single laser FACScan (Becton Dickinson Immunocytometry Systems).

At 4-5 weeks, active hematopoiesis is observed at many sites within the engrafted bones. After 6-8 weeks, most of the grafts looked similar to normal human fetal bone marrow associated with lymphopoiesis, myelopoiesis, erythropoiesis, and megakaryocytopoiesis in a high degree of cellularity. The yield of the cells from the grafts 4-16 weeks after implantation is approximately 10% of the input. Wright-Giemsa staining of these cells on cytospin preparations also reveals the typical morphology of lymphoid, myeloid or erythroid cells at different maturational stages. These signs of active hematopoiesis are observed in more than 90% of the bone grafts and continue to 16 weeks after implantation.

The human origin of hematopoietic cells within the grafts is confirmed by flow cytometry with either MEM-43 (an antibody specific for a common antigen of human cells) or Ly5.1 (reactive with mouse pan-leukocyte antigen). The replacement of the human bone marrow with mouse hematopoietic cells is observed in some of the grafts incubated in vivo for over 20 weeks.

The characteristics of the hematopoietic cell populations in the bone marrow are analyzed by light scattering profiles using flow cytometry. Four distinctive clusters of hematopoietic cells, i.e., lymphoid (R1), blastoid (R2), myeloid (R3), and mature granulocyte (R4) populations are revealed in normal fetal bone marrow by forward and side scattering distributions. Similar analyses with MEM-43 positive human cells recovered from the bone implants at various different time points after implantation are carried out. Cells recovered 2 weeks after implantation do not show clear cluster formation, indicating that these cells are of non-hematopoietic origin, while the human cells from grafts incubated longer than 4 weeks showed scattering profiles that are similar to those of normal fetal bone marrow cells. Thus, the kinetics of the appearance of human hematopoietic cells in the implanted bone detected by scatter analyses is found to be in accord with the histological observations.

The cell surface phenotypes of the nucleated hematopoietic cells in the grafts can be further analyzed with various antibodies specific for human lineage markers. About 80% of the cells in the lymphoid (R1) region are B cells, positive for both CD10 and CD19. When stained for surface immunoglobulin, about 20% express IgM and about 4% express IgD as well. The ratio of cells with either κ or λ light chains was similar to that in normal bone marrow, suggesting that these B cells are not products of a monoclonal expansion. A small number (<5%) of human T-lineage cells detected by CD7 antibody are found in this region. Approximately 60% of the cells in the myeloid (R3) region are found to express the CD15 antigen, specific for myelomonocytic cells, indicating that the major population of the cells in this region was the immature forms of myelomonocytic cells. Over 80% of the cells in the R4 region are also positive for this marker and the light scattering profile indicated that they are mature forms of granulocytes. The cell population in the blastoid (R2) region is a mixed population of $CD10^+$ $CD19^+$ cells, $CD15^+$ cells, and cells lacking these markers. Furthermore, as observed in normal fetal bone marrow, a significant (5-10%) number of cells in the R1 and R2 regions express CD34, a marker for bone marrow progenitor cells. Taken together, the cellular composition in each cluster in the implanted human bone marrow is found to be similar to those of normal fetal bone marrow.

The level of human erythropoietic activity is analyzed with antibodies specific for human glycophorin A (GPA). Flow cytometric analysis of human glycophorin A (GPA) expression in bone marrow cells from the grafts is performed. The cell suspensions are prepared from the grafts without ammonium chloride treatment. The cells are stained with biotinylated-anti-human GPA antibodies, followed by FITC-avidin binding as described above. After final washing with PBS, the cells are fixed in 2.5% paraformaldehyde in PBS, and then incubated with PI at the final concentration of 1 μg/ml to stain nuclear DNA.

Human progenitor cells with self-renewal and multi-lineage capacity are functionally maintained when human bone grafts are implanted into SCID mice. Kinetics of progenitor cell activities by colony forming assay in culture are examined.

The total number of colonies per graft is obtained by calculation based on the numbers of the colonies and the total cell number recovered. Bone grafts from different fetal donors are used for this experiment. CFU-GM and BFU-E are assayed by methylcellulose cultures, according to previously described methods. Briefly, the bone marrow cells are plated in, 24 well plates at a concentration of $1-5\times10^4$/ml in 0.25 ml cultures containing 1% methylcellulose in Iscove's modified Dulbecco's medium (Gibco Laboratories) with 20% FBS, 0.05 mM 2-mercaptoethanol, 200 mM L-glutamine, 0.8% lept-albumin, 0.08% $NaHCO_3$, and human recombinant erythropoietin (Amgen Biologicals) at the concentration of 2 u/ml, and 10% Mo conditioned media. The methylcellulose cultures are incubated at 37° C. in 7% $CO_2$ in air and are counted after 12 days to determine the number of colonies per well. CFU-C are characterized as having greater than 50 cells and consisted mainly of granulocytes and/or macrophages (CFU-GM) or multiple clusters of erythroid cells (BFU-E).

Finally, the presence of human cells in the peripheral circulation of SCID-hu mice with bone grafts is examined by FACS analysis, using the combination FITC-HLe1 antibody (the common human leukocyte antigen, CD45) and PE-W6/32 antibody (a monomorphic determinant of MHC-Class I).

Human cells are detected at significant frequency in peripheral blood from the SCID-hu mice examined after 9 weeks of implantation.

To determine the effect of a wnt inhibitor on human progenitors in the bone marrow, CB-17 scid/scid mice in which are implanted human fetal bone from various long bones 8 to 10 weeks before, are treated at various dose levels with a CRD-Ig molecule, as described in Example 1. The animals are treated with an initial dose of the CRD-Ig; and after two days, cells are recovered from implanted bones. The number of proliferating stem cells is calculated by staining for human, CD34+, Thy-1+ cells; and staining with Ki67 (a nuclear protein expressed in proliferating cells during late G1-, S-, M-, and G2-phases of the cell cycle, but not in the G0 (quiescent) phase). The number of actively proliferating stem cells is normalized to a control animal.

To test the ability of the stem cells to resume normal proliferation, the animals are treated with various doses of Wnt3A protein, 3 days after the administration of the CRD-Ig. The wnt protein acts to wash out the inhibitor, and allows resumption of normal signaling. Two days later, the stem cells are again collected, and tested for the presence of proliferating cells as described above.

In order to establish the protection of stem cells from anti-proliferative agents, a dose of CRD-Ig that is sufficient to block proliferation, but which does not prevent resumption of proliferation following a wnt washout, is administered to the animals. 12 hours later, the animals are treated with a single dose of methotrexate at a dose equal to the $LD_{50}$ for HSC. A control animal is treated with methotrexate in the absence of the protective CRD-Ig. After 24 hours, the stem cell viability is calculated in the absence, or presence of the protective agent, in a colony assay as described above.

Example 3

Growth and Metastasis of Human Leukemia Cells in an Animal Host

A SCID-hu animal model is set up for human bone marrow, and is further tested by the addition of human leukemia cells. The human HSCs are tested after induction of quiescence for the presence of non-proliferating cells; and for the resumption of normal hematopoiesis after the quiescent period. The cells are then tested for resistance to killing by anti-proliferative agents that target the proliferating leukemia cells.

Patient samples. Bone marrow (BM) samples from myeloid leukemia patients, including acute myeloid leukemia and chronic myeloid leukemia in myeloid blast crisis, are obtained with informed consent. Mononuclear cells are isolated by Ficoll-Paque (Pharmacia) density sedimentation and are then cryopreserved in RPMI-1640 (GIBCO) containing 10% DMSO and 10% fetal bovine serum (FBS). After thawing, cells are washed with RPMI-1640 containing 10% FBS and used for flow cytometric analysis and for implantation.

SCID-hu mice. Homozygous C.B-17 scid/scid mice (SCID) are bred, treated with antibiotics, and used when 6-8 week old. Femurs and tibias of 19 to 23 gestational week human fetuses are cut into fragments and implanted subcutaneously into the mice. Cell suspensions prepared from thymus of individual fetal donors are analyzed for the HLA allotypes.

Injection of leukemia cells. After thawing, bone marrow cells of leukemia patients ($0.4-2.0 \times 10^6$ viable cells) are resuspended in 20 ml of RPMI-1640 containing 10% FBS and injected with a microliter syringe (Hamilton Co.) directly into the human fetal bone grafts. The bone grafts are implanted subcutaneously 6-8 weeks prior to the injection of leukemia cells. Combinations of bone and leukemia donors are selected to be disparate for commonly distributed HLA allotypes so that the origin of the cells in human bone implant can later be traced.

Antibodies. Mouse monoclonal antibodies against MHC class I antigens are directly conjugated with either FITC or PE. FITC-anti-LeuM1 (CD15), PE-anti-LeuM9 (CD33), PE-anti-Leu12 (CD19), FITC-anti-CALLA (CD10), and FITC-anti-HLe1 (CD45) are purchased.

Flow cytometry. Single cell suspensions are prepared from human bones and/or tumors by mincing tissues with scissors in cold RPMI-1640 containing 10% FBS. Cells are then treated with ammonium chloride to lyse red blood cells and stained by immunofluorescence for the indicated markers Cells from mouse peripheral blood and bone marrow are examined as well. Before analysis, propidium iodide is added at a final concentration of 10 µg/ml to selectively gate out dead cells. Multiparameter flow cytometry is performed using the FACScan system. Percent leukemia cells is calculated as the percentage of patient's HLA allotype positive cells per total human cells in the individual samples. In each experiment, isotype-matched antibodies are included as negative controls.

Histology. Cytocentrifuge slides are prepared and stained with the Wright-Giemsa stain.

Implantation Of Human Myeloid Leukemia Cells Into SCID-Hu Mice. Cryopreserved BM cells from leukemia patients are directly injected into human fetal bone fragments of SCID-hu mice. The growth of human leukemia cells in injected human BM, as well as mouse BM, is analyzed by flow cytometry 4-56 weeks after injection.

In order to establish the protection of stem cells from anti-proliferative agents, a dose of CRD-Ig that is sufficient to block proliferation, but which does not prevent resumption of proliferation following a wnt washout, is administered to the animals. Twelve hours later, the animals are treated with a single dose of CPT-11 at a dose equal to the $LD_{50}$ for HSC. A control animal is treated with CPT-11 in the absence of the protective CRD-Ig. After 24 hours, the stem cell viability is calculated in the absence, or presence of the protective agent, in a colony assay as described above. The number of viable tumor cells is similarly calculated.

Example 4

Cells of human lung cancer cell lines are introduced intravenously into immunodeficient SCID mice implanted prior to inoculation with fragments of human fetal lung and human fetal bone marrow.

Mice and Tissues. Homozygous CB-17 scid/scid mice are used at the age of 6 to 8 weeks. Human fetal lungs at 18 to 22 gestational weeks are cut into fragments approximately 1 mm³ and surgically implanted into mouse mammary fat pads and under the kidney capsule. Human fetal femurs and tibias at the same gestational age are cut lengthwise and implanted subcutaneously into SCID mice. The resulting SCID-hu animals are used for experiments at 4 to 8 weeks post implantation.

Cell Lines. Small cell lung carcinomas (SCLC) cell lines N417 and H82 of variant subtype are obtained from National Cancer Institute, National Institutes of Health. Lung adenocarcinoma cell line A427 is obtained from ATCC. Cell lines are maintained in growth medium RPMI 1640 (N417 and H82) or DMEM (A427) supplemented with 10% fetal bovine serum.

Tumor cells are injected into SCID-hu mice intravenously via the lateral tail vein. Alternatively, cells are injected directly into human fetal tissues implanted subcutaneously into mice. Mice are examined twice a week for growth of tumors and sacrificed at or before the time when tumor volume reaches 5 cm$^3$. Human lung implants, mouse lungs and other internal organs and tumors are examined histologically. Single cell suspensions are prepared from the aseptically removed and minced tumors by incubation for 1 hour at 37° C. in the presence of dispase and DNase. Cells are washed and used for intravenous injection or explanted in vitro to reestablish cell lines.

In order to establish the protection of stem cells from anti-proliferative agents, a dose of CRD-Ig that is sufficient to block proliferation, but which does not prevent resumption of proliferation following a wnt washout, is administered to the animals. Twelve hours later, the animals are treated with a single dose of CPT-11 at a dose equal to the LD$_{50}$ for HSC. A control animal is treated with CPT-11 in the absence of the protective CRD-Ig. After 24 hours, the stem cell viability is calculated in the absence, or presence of the protective agent, in a colony assay as described above. The number of viable tumor cells is similarly calculated.

Example 5

Adenoviral expression of Dkk1 (Ad Dkk1) is used to achieve stringent, fully conditional and reversible Wnt inhibition in transgenic adult mice.

Methods

Ad Construction and Production. Dkk1 cDNA was amplified from embryonic day (E) 17.5 mouse embryo cDNA with C-terminal FLAG and/or His6 epitope tags, sequenced, and cloned into the E1 region of E1-E3-Ad strain 5 by homologous recombination, followed by Ad production in 293 cells and CsCl gradient purification of virus as previously described. The negative control virus Ad Fc expressing a murine IgG2a Fc fragment has been described.

Ad Administration and Detection of Plasma Transgene Expression. Adult (12-16 weeks old) male C57BL/6 or CB17 severe combined immunodeficient (SCID) mice received single i.v. tail vein injection of 10$^9$ pfu of the appropriate Ads. For low-dose studies, 3×10$^8$ plaque-forming units (pfu) were administered. At appropriate times after injection, whole blood was obtained by retroorbital phlebotomy followed by Western blot analysis of 1 µl of plasma using anti-His probe antibody (Santa Cruz Biotechnology) or anti-His C-term antibody (Invitrogen). Low-dose (3×10$^8$) administration was estimated to produce 10-20% of the circulating Dkk1 levels in high-dose animals (10$^9$ pfu).

Immunohistochemistry and Histology. The following antibodies were used: Rat anti-mouse CD44 (1:100; BD Pharmingen), rat anti-mouse Ki67 (1:100; DAKO), goat anti-mouse EphB2 (1:100; R & D Systems), rabbit anti-rat FABP (1:100; Novus Biologicals, Littleton, Colo.), and rabbit anti-human lysozyme (1:100; DAKO). Immunostainings of paraffin-embedded samples were performed according to standard procedures. Antigen retrieval was accomplished by boiling samples in Na-citrate buffer (10 mM, pH 6.0) for 20 min. Color development was performed by using diaminobenzidine (brown precipitate) with hematoxylin counterstain. For immunofluorescence, samples were cryoembedded in OCT compound and sectioned at 7-µM thickness. Stainings were visualized with Alexa 488-conjugated secondary anti-goat antibodies (Molecular Probes) and nuclei were counterstained with Hoechst 33342 (Molecular Probes). For histological analysis, hematoxylin/eosin and Alcian blue staining of paraffin-embedded sections was performed according to standard protocols. Gremelius staining was performed by using Pascual's modified method. Terminal deoxynucleotidyltransferase-mediated dUTP nick end labeling (TUNEL) staining on paraffin-embedded samples used 20 µM biotin-16-UTP and 0.4 units/µl terminal transferase followed by color development (Vectastain ABC kit, Vector Laboratories) and methyl green counterstaining.

Construction of Dkk1 Ads. Dkk1 cDNA was amplified from E17.5 mouse embryo cDNA by PCR, using the forward primer (SEQ ID NO:1) 5'-GAT CGG GGC CCA GCC GGC CAC CTT GAA CTC AGT TCT CAT CM T-3' and the reverse primer (SEQ ID NO:2) 5'-GAT CGG ATC CTC AAT GGT GAT GGT GAT GAT GCT TGT CAT CGT CGT CCT TGT AGT CGT GTC TCT GGC AGG TGT GGA GCC T-3', which incorporated C-terminal FLAG and His$_6$ epitope tags. The PCR product was cloned into pCR2.1 (Invitrogen), was sequenced and was subcloned SfiI-SalI as an in-frame fusion with the IgK signal peptide downstream of the human CMV promoter of the Ad shuttle plasmid, Add2 SecTag, a variant of Add2. For murine Dkk1-HA containing an N-terminal HA and C-terminal FLAG and His$_6$ epitope tags, the Dkk1A insert was excised SfiI-SalI and ligated in-frame into SfiI-SalI-cut Ad shuttle plasmid Add2 Display, a variant of Add2 containing a 5' IgK signal peptide and an HA tag. The Dkk1 and Dkk1-HA inserts were cloned into the E1 region of E1⁻E3⁻ Ad strain 5 as using homologous recombination, followed by Ad production in 293 cells and CsCl gradient purification of virus. The negative control virus Ad Fc expressing a murine IgG2a Fc fragment has been described by Kuo et al. (2001) *Proc. Natl. Acad. Sci. USA* 98, 4605-4610.

β-catenin Stabilization Assay. L cells were grown in DMEM containing 10% FBS and seeded in 24-well plates at a density of 2×10$^5$ cells per well. The cells were treated with 125 ng/ml Dkk1 purified over Ni-agarose from adenoviral supernatant for 2 h, after which purified Wnt3a protein was added for an additional 3 h (1:8,000). Cells were washed in PBS and lysed in TNT buffer (150 mM NaCl/50 mM Tris.HCl, pH 7.5/1% Triton X-100). The cell lysates were analyzed for β-catenin levels by using Western blotting and anti-β-catenin mAb (BD Transduction Laboratories, Stanford, Calif.).

Luciferase Reporter Assays. The 293T cells were seeded in 24-well plates at a density of 1×10$^5$ cells per well. Plasmids transfected are as follows (µg per well): pTOPFLASH, 0.1; EF-LacZ, 0.1; PGKWnt3a, 0.3; Add Dkk1, 0.3. Total DNA transfected was normalized to 0.8 µg per well by using PGK vector. Luciferase assays were performed using the Dual-Light reporter gene assay system (Tropix, Bedford, Mass.). Luciferase activity was normalized against β-galactosidase activity and all assays were performed in triplicate.

Quantitation of Proliferative Index. Ki67-positive epithelial cells were quantitated on 3-5 high-powered fields for each portion of the gastrointestinal tract. Fields were selected for similar tissue planes and an equivalent number of anatomic structures (e.g., villi) were analyzed on each field. The observer was blinded to the treatment conditions of the mice.

Results

To achieve conditional Wnt inactivation in adult animals, an Ad-expressing murine Dkk1 cDNA bearing C-terminal His6 and Flag epitope tags was produced (Ad Dkk1) by conventional methods. The transfected adenoviral Dkk1 shuttle plasmid inhibited Wnt3a-stimulated transcription of a TOPFLASH reporter gene, whereas recombinant Dkk1 purified from Ad Dkk1 supernatants inhibited recombinant Wnt3a-induced β-catenin stabilization in L cells, which is consistent with appropriate functional activity. Single i.v. injection of purified Ad Dkk1 (109 pfu) into tail veins of adult (12-16 weeks old) C57BL/6 mice resulted in liver transduction and produced transient Dkk1 expression in plasma peaking at day 2 and progressively diminishing over an 11-day period, which is in agreement with the typical expression kinetics of Ads in immunocompetent mice.

Single i.v. administration of Ad Dkk1 (109 pfu) to adult C57BL/6 mice produced progressive weight loss and frequent melena or hematochezia with >85% mortality by 10 days. An identical phenotype was observed with an independent Ad expressing an N-terminal hemagglutinin (HA)-tagged Dkk1 (Ad Dkk1-HA). In contrast, significant weight loss, gastrointestinal bleeding, or mortality were not observed with control Ads expressing either an Ig IgG2 Fc fragment (Ad Fc), the non-Wnt inhibitor Dkk3, or the soluble VEGF receptor, Flk1-Fc, at levels comparable to, or exceeding that of, Ad Dkk1. Ad Dkk1 doses of $3 \times 10^8$ pfu or lower produced progressively less precipitous weight loss and were not associated with either hematochezia, melena, or mortality over a 120-day time course.

The ease of preparation of Ad combined with the convenience of single-injection dosing facilitated examination of synchronized cohorts of Ad Dkk1-treated animals ($10^9$ pfu) over defined intervals of a 10-day time course. Mucosal architecture in duodenum and proximal jejunum was severely distorted with rapid and near-total loss of crypts and decreased villus density by days 2 and 4, without inflammation or crypt necrosis. In remnant crypts, Paneth cells predominated, and, by day 7, crypt loss was followed by villus blunting and fusion, loss of mucosal integrity, and frank ulceration and mucosal hemorrhage with mixed inflammatory infiltrate in the lamina propria. The small intestine exhibited a proximal-distal gradient of histologic effects with most severe phenotypes observed in duodenum and proximal jejunum, with the distal jejunum and ileum manifesting only mild crypt loss and villus blunting.

Figure 9:
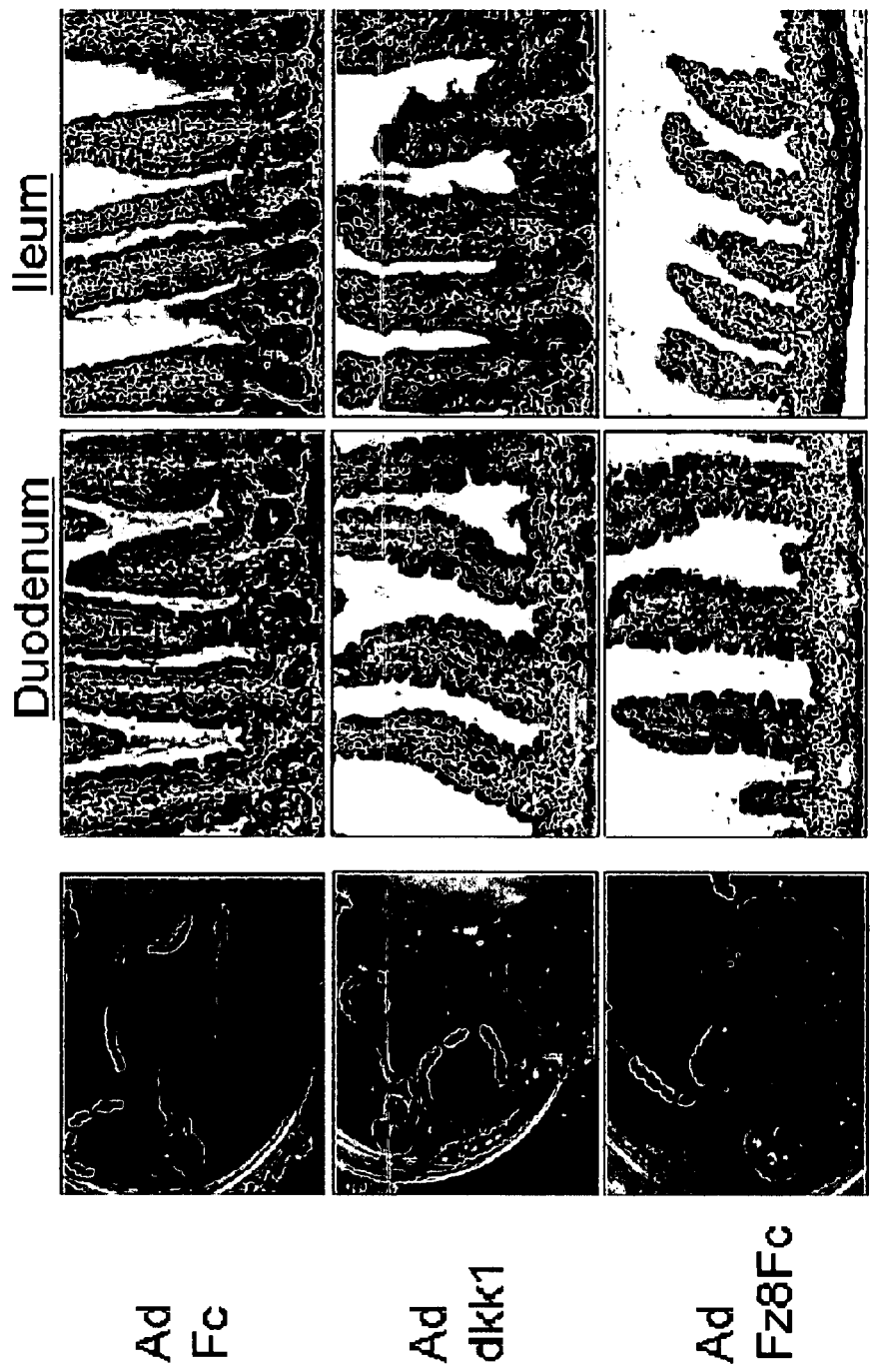
FIG. 9 shows the effects of different adenoviral vectors on the small bowel of a mouse after expression of the Wnt inhibitors.

In the colon and cecum of C57BL/6J mice, only mild glandular thinning and/or crypt loss was observed at days 2 and 4, which was in contrast to striking crypt loss and villus blunting in the small intestine. However, by day 7, the cecal and colonic epithelium exhibited multifocal mucosal degeneration and ulceration of a severity exceeding that of the small intestine, with the descending colon more severely affected than the ascending colon. The spectrum of colonic lesions ranged from noninvolved foci particularly in ascending colon, to mild glandular thinning, focal ulceration, and extensive areas with complete effacement of architecture and replacement with mixed inflammatory infiltrates. Ad Dkk1 treatment of CB17 SCID mice lacking B and T lymphocytes resulted in an identical spectrum of colon architectural lesions as in C57BL/6J mice, suggesting that the observed colitis in C57BL/6J mice was not inflammatory or autoimmune in nature. However, the ascending colon was more severely affected in SCID than C57 with more extensive and ulcerated lesions (FIG. 9), which was potentially consistent with higher level and more persistent adenoviral gene expression in immunocompromised SCID mice. Similarly, rectums of Ad Dkk1-treated SCID mice exhibited frequent ulceration as opposed to mild glandular thinning in C57BL/6J mice. In contrast to the profound changes in small intestine and colon, the stomach of both strains exhibited only moderate glandular thinning at late time points that could not be distinguished from gastric atrophy secondary to inappetance. Ad Dkk1 small intestine phenotypes were identical in both C57BL/6J and SCID mice, with severe involvement of duodenum and jejunum and notable absence of pathology in ileum. A summary table of gastrointestinal phenotypes in C57BL/6J and SCID mice is presented in Table 1.

TABLE 1

Summary of severity and penetrance of gastrointestinal phenotypes induced by Ad Dkk1

| | C57BL/6 | | SCID | |
|---|---|---|---|---|
| | Severity | Penetrance | Severity | Penetrance |
| Stomach | – | 8/8 | – | 6/6 |
| Duodenum | +++ | 11/12 | +++ | 8/8 |
| Jejunum | +++/++ | 12/12 | +++ | 8/8 |
| Ileum | + | 6/12 | + | 7/8 |
| Cecum | +++ | 9/9 | +++ | 6/6 |
| Ascending colon | ++ | 8/9 | +++ | 5/6 |
| Descending colon | +++ | 9/9 | +++ | 6/6 |

–, unaffected.
+, minimal changes; e.g., increase in individual necrotic cells, mild villus blunting.
++, moderate changes, typically moderate reduction in crypt/gland numbers without other changes or mild multifocal ulceration in a background of healthy hyperplastic mucosa.
+++, severe changes, typically severe ulceration with associated inflammation, with or without hyperplasia.

Animals treated with lower doses of Ad Dkk1 ($3 \times 10^8$ pfu) exhibited 80% lower plasma levels and displayed a less severe intestinal phenotype relative to high-dose ($10^9$ pfu) animals, illustrating dose dependency of Ad Dkk1. In these lower-dose animals, decreased small intestine crypt density with overall intact mucosal architecture was observed at day 4 in duodenum but not jejunum and ileum. In cecum and colon of low-dose animals, ulceration, edema, and inflammation were less severe than with high-dose, and these animals did not exhibit mortality over a 120-day time course.

In both small and large intestine, decreased adenoviral transgene expression at day 10 was accompanied by epithelial regeneration, which was consistent with a reversible effect. By day 10, duodenum and jejunum exhibited small numbers of regenerative basophilic, hyperplastic crypts, with more advanced reconstitution of villus structure in jejunum than duodenum. In day 10 colon, hyperplastic regenerative crypts coexisted with persistent multifocal mucosal ulceration. Despite this regenerative response, frequent mortality was observed with high doses of Ad Dkk1 ($10^9$ pfu) at days 8-10, which was likely secondary to colitis and systemic infection, with elevated WBC counts ($>20 \times 10^3/\mu l$) and a left-shifted differential commonly noted in premorbid mice. Examination of adherens junctions in nonulcerated areas by electron microscopy and by immunofluorescence did not reveal significant alterations, whereas histologic examination of other solid organs including liver revealed them to be unaffected in a Dkk1-specific fashion, except for thymic atrophy, which could not be distinguished from systemic illness.

Figure 10:
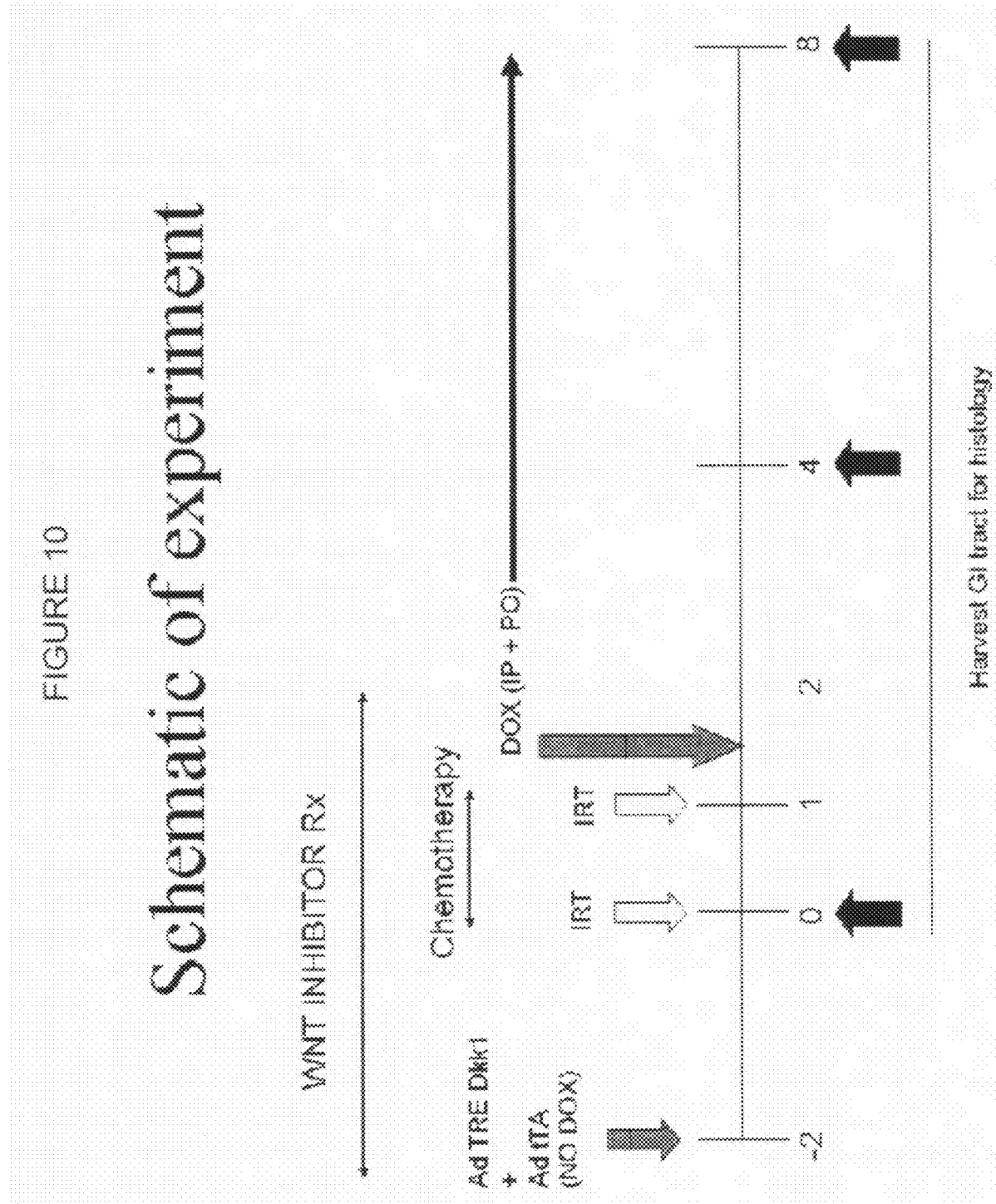
FIG. 10 is a protocol schematic for chemotherapy using Wnt inhibition to protect normal cells.

Confirming functional blockade of canonical Wnt signaling by Dkk1, the β-catenin/TCF target gene, CD44, was strongly and rapidly repressed within 2 days in duodenum and jejunum, with only nonepithelial lamina propria staining remaining (FIG. 10). Ad Dkk1 also potently repressed CD44 expression in ileum, despite the lack of gross architectural changes. Epithelial CD44 expression was markedly reduced by Dkk1 in cecum and distal colon and partially reduced in proximal colon but was unaffected in stomach. Dkk1 also repressed the β-catenin/TCF target gene, EphB2, in duodenum, jejunum, ileum, cecum, and descending colon, with mild repression in ascending colon, and little to no repression in stomach. In contrast, the magnitude or location of expression of epithelial differentiation markers for absorptive enterocytes or secretory lineages was not altered by Dkk1 expression.

The proliferative status of the gastrointestinal epithelium in Ad Dkk1 mice was examined by immunohistochemistry for the S-phase marker, Ki67. Ad Dkk1 strikingly repressed enterocyte Ki67 immunoreactivity (>90%) within 2-4 days in duodenum and proximal jejunum, with any remnant crypts exhibiting diminished Ki67 staining and residual expression largely confined to nonepithelial cells of the lamina propria. Proliferation in jejunum, along the proximal-distal axis, was progressively less affected by Ad Dkk1 to the extent that Ki67 staining in the ileum was not significantly inhibited by Ad Dkk1, despite effective repression of CD44 and EphB2 expression. Epithelial Ki67 staining was also substantially reduced (7080%) in cecum and descending colon, moderately reduced in ascending colon (60%), and not significantly affected in stomach. In contrast, TUNEL staining did not reveal increased apoptosis in either the proliferative crypts or differentiated villi/glands of the stomach, small intestine or colon. In total, these data indicated that Dkk1 elicited stringent in vivo blockade of canonical Wnt signaling in both small intestine and colon, with repression of both Wnt target gene expression and epithelial proliferation in parallel.

We have achieved stringent, fully conditional and reversible inactivation of Wnt signaling in adult mice by adenoviral expression of the soluble Wnt inhibitor Dkk1, which functions as a pan-inhibitor of canonical Wnt signaling through interactions with the Wnt coreceptors, LRP5/6. The extensive Ad Dkk1 repression of proliferation and of β-catenin/TCF target genes, as well as the progressive loss of villi and glands in small intestine, cecum, and colon to the point of mucosal ulceration, implicates the Wnt receptor complex and canonical Wnt signaling in maintenance of gene expression and architecture throughout the intestinal epithelium, which is consistent with, but much more extensive than, the mild reduction of villus number in Tcf4–/– mouse small intestine. The additional colon and cecum phenotypes observed in Dkk1 mice could result from either Dkk1 membrane-proximal interference with Wnt signaling versus membrane-distal effects in Tcf-4–/– animals, or from Tcf-3/Tcf-4 redundancy. Analogous mechanistic redundancy with non-Wnt- or non-Dkk1-sensitive pathways may underlie the observed proximal-distal phenotypic gradient in Ad Dkk1 small intestine, as well as the Dkk1 inhibition of Wnt target gene expression but not proliferation in ileum. Given the direct action of Dkk1 on the LRP/frizzled receptor complex, as opposed to the membrane-distal action of Tcf-4, the current data demonstrate Dkk1-sensitive Wnt signaling as essential for maintenance of both proliferation and architecture of the intestinal epithelium in adult animals.

The current data, using a distinct, fully conditional adenoviral approach, suggest a broad physiologic role for Wnt signaling in the adult gastrointestinal tract that is not restricted to the small bowel, but is a general property of the intestinal glandular epithelium, whether in small intestine or colon.

Example 6

Fz8-Fc, a synthetic Wnt inhibitor, is a chimeric protein containing the Wnt-binding cysteine-rich domain (CRD) of the extracellular portion of the Fz8 (Frizzled-8) receptor fused to the constant region (Fc) of immunoglobulin (mouse IgG2a) heavy chain. Unlike Dkk1, which removes the co-receptor for canonical Wnt signaling (LRP5/6) from the cell surface, Fz8-Fc inhibition of Wnt signaling is mediated by sequestration of Wnt ligand. Ad Fz8-Fc ($10^9$ pfu) given as a single I.v. dose resulted in rapid lethality (4-5 days) in adult C57Bl/6 mice. Histopathologic examination of these Fz8-Fc treated animals reveals abolishment of the proliferative crypts of the intestinal epithelium throughout the entirety of the small bowel. These results with Ad Fz8-Fc corroborate those seen with systemic expression of Dkk1, albeit with a fully distinct mechanism of Wnt inhibition, and further extend those results to demonstrate a broader requirement for Wnt signaling in the intestinal epithelium. The greater potency of Fz8-Fc in vivo reflects its superior pharmacokinetics when compared to Dkk1, as both proteins exhibit similar potency in cell culture against stimulation of Wnt signaling mediated by Wnt3a. In mice, recombinant Fz8-Fc administered i.v. demonstrates a serum-life of approximately 20 hours, while Dkk1 has a serum half-life of approximately 10 minutes. These pharmacokinetic properties of recombinant Fz8-Fc protein are desirable for in vivo therapeutic applications of the present invention.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for protection of normal intestinal cells from cytotoxic therapy that targets proliferating cells, the method comprising:

contacting said normal intestinal cells with an adenoviral expression vector comprising Dickkopf (Dkk) coding sequences; for a period of time sufficient to block wnt signaling in normal cells;

contacting said normal cells with a cytoreductive topoisomerase inhibitor therapy;

wherein normal cells dependent on wnt signaling for proliferation are protected from said cytoreductive therapy.

2. The method of claim 1, wherein said normal cells are present in a tissue with familial adenomatous polyposis coli (FAP) cancer cells.

3. The method of claim 2, wherein said cancer cells have a mutation in adenomatosis polyposis coil (APC).

* * * * *

SEQUENCE LISTING

```
<160> NUMBER OF SEQ ID NOS: 2

<210> SEQ ID NO 1
<211> LENGTH: 43
<212> TYPE: DNA
<213> ORGANISM: mouse

<400> SEQUENCE: 1
gatcggggcc cagccggcca ccttgaactc agttctcatc aat            43

<210> SEQ ID NO 2
<211> LENGTH: 79
<212> TYPE: DNA
<213> ORGANISM: mouse
```

```
<400> SEQUENCE: 2
gatcggatcc tcaatggtga tggtgatgat gcttgtcatc gtcgtccttg tagtcgtgtc    60
tctggcaggt gtggagcct                                                 79
```